United States Patent
Gaskill-Shipley et al.

(10) Patent No.: US 12,412,272 B2
(45) Date of Patent: Sep. 9, 2025

(54) CHARACTERIZING INTRA-SITE TUMOR HETEROGENEITY

(71) Applicants: University of Cincinnati, Cincinnati, OH (US); Children's Hospital Medical Center, Cincinnati, OH (US)

(72) Inventors: Mary Gaskill-Shipley, Cincinnati, OH (US); Jinghua Wang, Mason, OH (US); Lili He, Mason, OH (US)

(73) Assignees: UNIVERSITY OF CINCINNATI, Cincinnati, OH (US); CHILDREN'S HOSPITAL MEDICAL CENTER, Cincinnati, OH (US)

( * ) Notice: Subject to any disclaimer, the term of this patent is extended or adjusted under 35 U.S.C. 154(b) by 588 days.

(21) Appl. No.: 17/777,457

(22) PCT Filed: Nov. 24, 2020

(86) PCT No.: PCT/US2020/061975
§ 371 (c)(1),
(2) Date: May 17, 2022

(87) PCT Pub. No.: WO2021/108382
PCT Pub. Date: Jun. 3, 2021

(65) Prior Publication Data
US 2022/0405932 A1    Dec. 22, 2022

Related U.S. Application Data

(60) Provisional application No. 62/940,311, filed on Nov. 26, 2019.

(51) Int. Cl.
*G06T 7/00* (2017.01)
*A61B 5/00* (2006.01)
(Continued)

(52) U.S. Cl.
CPC .......... *G06T 7/0014* (2013.01); *A61B 5/0042* (2013.01); *A61B 5/055* (2013.01);
(Continued)

(58) Field of Classification Search
CPC ......... G06T 7/0014; G06T 7/11; G06T 7/168; G06T 7/0012; G06T 2207/10096;
(Continued)

(56) References Cited

U.S. PATENT DOCUMENTS 9,235,887 B2 *  1/2016  Buckler ................. G06T 7/143
10,429,393 B2   10/2019 Bapat et al.
(Continued)

FOREIGN PATENT DOCUMENTS

WO    2013130714 A1    9/2013
WO    2017079695 A1    5/2017
(Continued)

OTHER PUBLICATIONS

Gillies, et al., "Radiomics: images are more than pictures, they are data", in Radiology. 2016;278:563-577.
(Continued)

*Primary Examiner* — John B Strege
(74) *Attorney, Agent, or Firm* — Dinsmore & Shohl LLP

(57) ABSTRACT

A method and a system for measuring intra-site heterogeneity in a tumor using magnetic resonance imaging (MRI). The method includes acquiring magnetic resonance (MR) images using MRI modality; segmenting tumor sites in the MR images; dividing each of the tumor sites into a plurality of sub-regions; deriving image biomarkers from each voxel or pixel in the plurality of sub-regions; classifying each voxel or pixel in the plurality of sub-regions into genotypes or molecular subtypes based on the extracted image biomarkers and a classifier model including associations between image biomarkers and molecule sub-
(Continued)

types; creating a distribution of genotypes or molecular subtypes in the each of the plurality of sub-regions based on classifications of voxels or pixels; generating spatial information of genotypes or molecular subtypes in the tumor sites based on the distribution; and measuring intra-site heterogeneity in the tumor sites.

20 Claims, 13 Drawing Sheets

(51) Int. Cl.
  *A61B 5/055*   (2006.01)
  *G06T 7/11*   (2017.01)
  *G06T 7/168*   (2017.01)
(52) U.S. Cl.
  CPC .............. *A61B 5/4064* (2013.01); *G06T 7/11* (2017.01); *G06T 7/168* (2017.01); *G06T 2207/10096* (2013.01); *G06T 2207/20056* (2013.01); *G06T 2207/30016* (2013.01); *G06T 2207/30096* (2013.01)
(58) Field of Classification Search
  CPC . G06T 2207/20056; G06T 2207/30016; G06T 2207/30096; G06T 2207/10088; G06T 2207/20021; G06T 2207/20081; G06T 2207/20084; A61B 5/0042; A61B 5/055; A61B 5/4064; G16H 50/30; G16H 30/40
  See application file for complete search history.

(56) References Cited

U.S. PATENT DOCUMENTS

| | | | |
|---|---|---|---|
| 10,716,867 B2 | 7/2020 | De La Zerda et al. | |
| 11,288,806 B2* | 3/2022 | Mostapha | G16H 30/20 |
| 2015/0227687 A1* | 8/2015 | Mroz | G16B 30/00 |
| | | | 702/19 |
| 2017/0071496 A1* | 3/2017 | Gillies | A61B 5/7264 |
| 2017/0103525 A1* | 4/2017 | Hu | G06T 7/0012 |
| 2018/0321247 A1 | 11/2018 | Dittamore et al. | |
| 2019/0005640 A1 | 1/2019 | Shanbhag et al. | |
| 2019/0156159 A1* | 5/2019 | Kopparapu | G06F 18/24147 |
| 2019/0320934 A1* | 10/2019 | Odry | A61B 5/7264 |
| 2019/0367993 A1 | 12/2019 | Dai | |
| 2020/0275857 A1* | 9/2020 | Lou | G01R 33/50 |
| 2021/0071270 A1* | 3/2021 | Murillo | G01N 33/57415 |
| 2022/0164959 A1* | 5/2022 | Mostapha | G06N 3/045 |

FOREIGN PATENT DOCUMENTS

| | | |
|---|---|---|
| WO | 2019155050 A1 | 8/2019 |
| WO | 2019165475 A1 | 8/2019 |

OTHER PUBLICATIONS

Hu, et al., "Radiogenomics to characterize regional genetic heterogeneity in glioblastoma", in Neuro-Oncology 2016;19(1): 128-137.
Katiyar, et al., "Spectral Clustering Predicts Tumor Tissue Heterogeneity Using Dynamic 18F-FDG PET: A Complement to the Standard Compartmental Modeling Approach." In Journal of Nuclear Medicine 2017;58: 651-657.
Beer, et al., "Integration of proteomics with CT-based qualitative and radiomic features in high-grade serous ovarian cancer patients: an exploratory analysis" in European Radiology 2020;30(8): 4306-4316.
International Search Report mailed Feb. 11, 2021 in reference to co-pending Application No. PCT/US2020/061975 filed Nov. 24, 2020.

* cited by examiner

CHARACTERIZING INTRA-SITE TUMOR HETEROGENEITY

CROSS-REFERENCE TO RELATED APPLICATION

This application is a national phase of International Application No. PCT/US2020/061975filed on Nov. 24, 2020, which claims benefit of U.S. Provisional Application No. 62/940,311 filed on Nov. 26, 2019, the entire contents of which is incorporated by reference.

FIELD OF THE INVENTION

The present invention generally relates to the field of oncology and provides novel methods for identification, quantification, monitoring and analysis of intra-tumor heterogeneity using MRI images. More specifically, the present invention focus on the use of image biomarkers for characterizing intra-tumor heterogeneity within a brain tumor site. The invention is particularly useful in precision medicine of brain tumor.

BACKGROUND

There are more than 18 million cancer cases and over 8 million people die of cancer around the world each year. The global market for cancer therapies is projected to reach US$220. 5 billion by 2025. Despite tremendous efforts to cancer therapy over the past decades, overall cancer mortality remains high and has not changed substantially. The cancer therapy is mainly challenged by heterogeneity that is a hallmark of tumors and has a crucial role in the outcome of the malignancy, because it strongly impacts diagnosis at the genetic and molecular level and challenges the design of effective therapies. There are two types of heterogeneity: inter-tumor and intra-tumor heterogeneity. Specially, intra-tumor heterogeneity closely associates with cancer progression and contributes to cancer drug resistance, leading to the failure of many new therapies to deliver meaningful survival benefits and the increase in the health economic cost of therapeutic development. Therefore, the understanding of intra-tumor heterogeneity is very important for both research on fundamental mechanisms of tumor evolution and clinical practices of cancer treatment. For example, isocitrate dehydrogenase (IDH)-mutant GBMs are characterized by significantly improved survival than IDH-wild GBMs (31 months vs. 15 months). Recently, the US has considered personalized precision medicine based on genetic and molecular characterization of cancer as a national priority.

Currently, the methods for identifying intra-tumor heterogeneity includes invasive surgical biopsy and minimally invasive or non-invasive methods. A DNA sequence based on biopsy is a gold standard to identifying the intra-tumor heterogeneity. The intra-tumor heterogeneity is performed by measuring genetic information of tumor sample that are extracted from biopsy tissue. Systems and/or methods for measuring the intra-tumor heterogeneity from invasive surgery specimens are described in prior art:

International Publication No. WO 2014/055635 and U.S. Patent Application Publication No. US 20150227687 A1 to Edmund A. Mroz and James W. Rocco disclose systems and methods for identifying intra-tumor heterogeneity based on genetic information of a tumor sample.

International Publication No. WO 2015/107499A1 and U.S. U.S. Pat. No. 10,429,393B2 to Sharmila A. Bapat and Rutika R. Naik disclose flow cytometry methods to identify, quantify, and monitor intra-tumor heterogeneity based on cancer cell lines.

International Publication No. WO 2018/156904A1 and U.S. Patent Application Publication No. US 20190367993A1 to Donghai Dai disclose a method to identify driver mutations in a tumor and its cancer cell subpopulations based on specimens that are obtained from a tumor mass and from normal tissue. The invention is used to design treatment strategies for cancer patients.

However, surgical biopsy is often invasive, costly, and potentially harmful to patients. For example, some tissue biopsy, such as brain and pancreatic cancer, is associated higher risk for the patient. Additionally, even when genetic and molecular characterization is measured from tissue sampling, samples may not be accurate for the entire tumor because of a small portion of a heterogeneous tumor with inherent selection bias during tissue biopsy.

In order to address the drawback of tissue biopsy, the minimally invasive methods—liquid biopsy have proposed to characterize the intra-tumor heterogeneity. The liquid biopsy samples blood and other body fluids. Liquid biopsy is a relatively simple to obtain, making them less invasive and less expensive method which can be used for diagnosis, treatment stratification, and follow-up monitoring. Systems and/or methods for measuring the intra-tumor heterogeneity from minimally invasive liquid biopsies are described in prior art:

International Publication No. WO 2013/130714 A1 discloses systems and devices for multiple single cell capturing and processing utilizing microfluidics. Embodiments of the micro fluidic device are configured to capture single cells at discrete locations (niches). Said niches comprise a small gap such that a cell entering the niche blocks the gap and prevents any further flow into the niche. The niche gap is sufficiently small that cells may be captured at the operational pressure/flow level. A buffer inlet may converge with a cell inlet so as to force cells to a side of a feeder channel that is closest to a series of transverse cell capture channels. The resistance for the transverse cell capture channels may be lower than that of a cell overflow channel to induce preferential flow of cells into niches versus into the cell overflow channel. A fluidic connection or the niche gaps to an auxiliary chamber for processing/analyzing constituents of the captured cells is not disclosed.

International Publication No. WO 2017/079139A1 and U.S. Patent Application Publication No. US 20180321247 A1 to Ryan Dittamore and Dena Marrinucci disclose a method of detecting heterogeneity of disease in a cancer patient based on circulating tumor cells of a blood sample.

International Publication No. WO 2017.079695 A1 to Douglas J Jolly et al. discloses methods for classifying cancer indications into phenotypic subtypes for assigning a predictive response to therapy.

International Publication No. WO 2018/222979 A1 and U.S. Patent Application Publication No. US 20190367993 A1 to Ryan Dittamore disclose a method of detecting heterogeneity of metastatic disease in a cancer patient based on circulating tumor cells of a blood sample.

International Publication No. WO 2019/155050 A1 to Fergal Casey et al. discloses a method for identifying a cancer patient as likely to positively respond to a therapy regimen based on a solid tumor sample and/or a blood plasma sample.

Most biopsy-based methods, including tissue and fluid biopsies, are limited by sampling bias because of the heterogeneous nature of tumors and tumor sample bias. Additionally, biopsy-based methods are relatively long turn-round time, expensive, minimally invasive, and require large amounts of tissue or tissue analyses. Non-invasive medical imaging is a cost-effective alternative to tumor biopsies when these biopsies are associated with significant risk, tumor tissue is insufficient or inaccessible, and/or serial assessment of tumor molecular abnormalities is needed to optimize treatment. Medical imaging can provide non-invasive, real-time, inexpensive, and timely information about intra-tumor heterogeneity, which is not subject to sampling bias and artifact. Unlike biomarker testing from a biopsy, medical imaging can represent the phenotype of the entire and multiple tumors in 3 dimensions (3D). Systems and/or methods for measuring the intra-tumor heterogeneity from non-invasive medical images are described in prior art:

The paper "Radiomics: images are more than pictures, they are data" in Radiology. 2016; 278:563-577 to Robert J. Gillies et al. discloses a method to improve diagnostic, prognostic, and predictive accuracy using quantitative image feature derived from first-, second-, and higher-order statistics of radiological images.

The paper "Radiogenomics to characterize regional genetic heterogeneity in glioblastoma" in Neuro-Oncology 2016; 19(1): 128-137 to Leland S Hu et al. applies MRI-based texture analysis to characterize regional genetic heterogeneity throughout MRI-enhancing and non-enhancing tumor segments.

International Publication No. WO 2016/127039A2 and U.S. Pat. No. 10,716,867B2 to Zerda Adam De La et al. disclose an optical imaging method to detect intra-tumor heterogeneity, measure tumor drug response, and determine tumor surgical margin detection.

The paper "Radiogenomics to characterize regional genetic heterogeneity in glioblastoma" in Neuro Oncology 2017; 19:128-137 to Leland S. Hu et al discloses a method to predict underlying tumor molecular alterations using hand-crafted features derived from textural metrics.

The paper "Spectral Clustering Predicts Tumor Tissue Heterogeneity Using Dynamic 18F-FDG PET: A Complement to the Standard Compartmental Modeling Approach." In Journal of Nuclear Medicine 2017; 58: 651-657." to Prateek Katiyar et al. discloses a spectral clustering method for quantifying tumor heterogeneity using dynamic PET studies.

International Publication No. WO 2019/009954A1 and U.S. Patent Application Publication No. US20190005640A1 to Dattesh Dayanand Shanbhag et al. disclose approach employing a generic methodology for transforming individual modality specific multi-parametric data into data, e.g., maps or images, which provides direct insight into the underlying physiology of the tissue. This may facilitate better clinical evaluation of the disease data as well as help non-imaging technologists and scientist to directly correlate imaging findings with basic biological phenomenon being studied with imaging.

International Publication No. WO 2019/165475A1 to Leland S. Hu et al. discloses systems and methods for image-guided tissue analysis, MRI-based computational modeling, and imaging informatics to analyze the diversity and dynamics of molecularly—distinct subpopulations and the evolving competitive landscapes in glioblastoma.

The paper "Integration of proteomics with CT-based qualitative and radiomic features in high-grade serous ovarian cancer patients: an exploratory analysis" in European Radiology 2020; 30(8): 4306-4316 to Lucian Beer et al. discloses a method for applying radiomic features for characterizing intra-site tumor heterogeneity.

Despite the recent explosion of interest toward cancer evolution and spatial as well we temporal intra-tumor heterogeneity, this field still remains unclear. There is the little study identifying the intra-tumor heterogeneity within a tumor site using quantitative image biomarkers, more specificity in primary brain tumor and brain metastases.

SUMMARY

It should be understood that the invention is not limited in its application to the following description or illustrated in the drawings. The invention is capable of other embodiments or of being practiced in various ways. Additionally, it should be understood that the terminology herein is for the purpose of description and should not be regarded as limiting.

The present disclosure provides a method for identifying intra-tumor heterogeneity within a tumor site using the quantitative image biomarkers. This disclosure describes method and system to characterize intra-tumor site heterogeneity in brain cancer by quantitative image biomarkers derived from acquired MRI images. The images are acquired with one or more of MRI image modality, including, but not limited to, T1-weighted imaging, T2-weighted imaging, diffusion, diffusion tensor imaging, susceptibility-weighted imaging, perfusion-weighted imaging, chemical shift imaging, and intra-voxel incoherent motion, with and/or without the administration of contrast agent.

In one embodiment, a method for measuring regional intra-tumor heterogeneity in a brain tumor site using magnetic resonance imaging. The method includes: acquiring one or more magnetic resonance (MR) images of a region of interest including the tumor using at least one MRI modality; segmenting one or more tumor sites in the MR images; dividing each of the one or more tumor sites into a plurality of sub-regions; deriving image biomarkers from each voxel or pixel in each of the plurality of sub-regions; classifying each voxel or pixel in each of the plurality of sub-regions into one of genotypes or molecular subtypes based on the extracted image biomarkers and a classifier model including associations between image biomarkers and genotypes or molecule subtypes; creating a distribution of genotypes or molecular subtypes in the each of the plurality of sub-regions based on classifications of voxels or pixels in each of the plurality of sub-regions; generating spatial information of genotypes or molecular subtypes in the tumor sites based on the distribution of the genotypes or molecular subtypes in the plurality of sub-regions; and measuring intra-site heterogeneity in the tumor sites based on the spatial information.

In some implementations, the image biomarkers include tissue properties or image features, wherein the image features include at least one of size and shape based—features, descriptors of the image intensity histogram, descriptors of the relationships between image voxels including a gray-level co-occurrence matrix (GLCM), run length matrix (RLM), size zone matrix (SZM), and neighborhood gray tone difference matrix (NGTDM) derived textures, textures extracted from filtered images, and fractal features.

In some implementations, the classifier model comprises one or more of machine learning models, including support voting machine (SVM), a naive Bayes classifier, a decision tree, a boosted tree, a random forest classifier, a fuzzy logic classifier, a neural network, a nearest neighbor classifier, deep learning, and a nonlinear classifier.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

It is to be understood that this disclosure is not limited in its application to the details of construction and the arrangement of the components set forth in the following description or illustrated in the drawings. The invention is capable of other embodiments or of being practiced or carried out in various ways. Also, it is to be understood that the terminology employed herein is for the purpose of description and should not be regarded as limiting.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1:
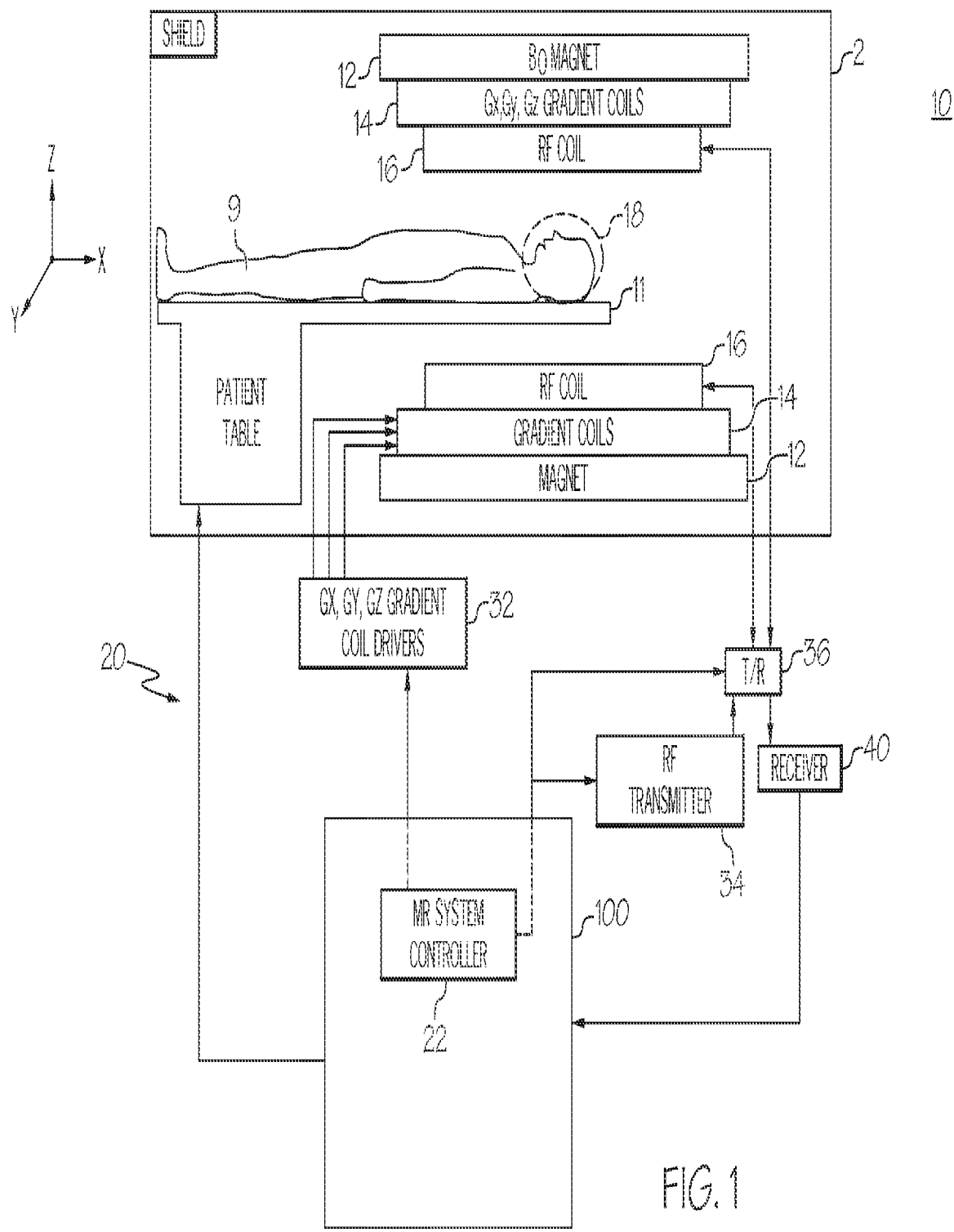
FIG. 1 is a diagram illustrating an example MRI system of image modalities, according to one or more embodiments shown and described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise.

The term "comprising" and variations thereof as used herein is used synonymously with the term "including" and variations thereof and are open, non-limiting terms.

The terms "optional" or "optionally" used herein mean that the subsequently described feature, event or circumstance may or may not occur, and that the description includes instances where said feature, event or circumstance occurs and instances where it does not.

The term "sample" as used herein refer to a tissue sample. It includes a specimen or culture obtained from any source. The samples obtained from human include, but are not limited to blood products, such as plasma, serum and the like.

The term "subject", "patient" or "object" as used herein interchangeably, means any a human. In some embodiments, the subject may be a human subject at risk for developing or already having cancer.

The term "heterogeneity" as used herein refers to the variations of the tumor cell's phenotype at genetic or molecular level. The tumor heterogeneity may divided into inter-tumor and intra-tumor heterogeneity.

The term "inter-tumor heterogeneity" as used herein indicates distinct morphological and phenotypic profiles among individual tumors at genetic or molecular level. For example, studies indicate that there exists inter-tumor heterogeneity of a breast cancer and its brain metastases. That is, there are a lot of different gene expression or genetic mutations between the breast cancer and its brain metastases.

The term "intra-tumor heterogeneity" as used herein refers to genetic or molecule phenotype heterogeneity among the cells of a tumor, which varies across the cells in a given tumor over time and space, including cells within a single site and cells from separated tumor sites. The intra-tumor heterogeneity may divided into inter-site and intra-site heterogeneity. The intra-tumor heterogeneity has adversely impact on treatment outcomes. For example, breast cancer brain metastases can be divided into three molecular subtypes (luminal, HER2 and triple negative subtypes) depending on the presence or absence of hormone receptor expression and certain other markers.

The term "inter-tumor site heterogeneity" as used herein to genetic or molecule phenotype heterogeneity among different tumor sites of a tumor.

The term "intra-tumor site heterogeneity" as used herein to genetic or molecule phenotype heterogeneity within a tumor site.

The terms "cancer" and "tumor" as used interchangeably herein, refer to cell growth that spreads to surrounding tissues, though the word tumor simply refers to a mass and a cancer is a particularly threatening type of tumor. The cancer indicates the physiological or pathological condition in which a population of cells are characterized by unregulated cell growth. A tumor is not necessarily a cancer.

The term "liquid biopsy" and variations thereof as used herein indicate a tool to detect molecules or cells in body fluids, such as peripheral blood, urine, saliva, cerebral spinal fluid, and breast milk.

The term "multiregional sampling" and variations thereof as used herein indicate sampling multiple areas within a single tumor site to determine the extent of gene and or molecule phenotype heterogeneity.

The term "biopsy sampling bias" and variations thereof as used herein indicates the inaccuracy of characterizing genetic and molecular profiles at a given site resulting from selective sampling of a single or limited number of regions.

The term "radiomics" as used herein is defined as the conversion of radiological images to higher dimensional image features and the subsequent mining of these data for medical practices. For example, the radiomics can identify tumor phenotype from anatomic or functional images at molecule or genetic or cellular levels by using the image features that are invisible by the naked eyes, including first and higher order statistics, fractal and shape features.

The term "radiogenomics" as used herein refers to the relationship between the imaging characteristics of a disease and its gene expression patterns, gene mutations, and other genome-related characteristics. Radiogenomics has a potential to study the cancer genomics without using invasive biopsy such as a surgery specimen.

The terms "therapy" and "treatment" as used interchangeably herein, refer to an intervention performed with the intention of improving a subject's status. For example, the term "Treatment" or "therapy" and their variation herein for cancer indicate inhibiting further cancer growth, and thereby causing shrinkage of a cancer. The treatment of cancer or cancer includes, but not limit to, surgery, chemotherapy, radiation therapy, hormonal therapy, immunotherapy, targeted therapy, stem cell transplants, precision medicine, anti-cancer drug, and their combinations.

The terms "target therapy" and "personalized medicine" as used interchangeably herein, refer to a type of cancer treatment that uses specific drugs or therapy techniques to precisely identify and attack specific types of cancer cells according to an individual's genetic or molecular profile. For example, the use of anti-HER2 therapy (trastuzumab and pertuzumab) has significantly prolonged the survival of breast cancer patients.

The term "artificial intelligence (AI)" as used herein refers to a computer performing tasks commonly associated with human intelligence. Humans can code and program a computer based on an algorithm or model to conduct the computer how to act, reason, and learn.

The term "machine learning" as used herein refers to a type of AI that sample data, known as "training data", are used to develop an algorithm or model in order to make predictions or decisions. Generally, the more data a machine learning model is exposed to, the better it performs over time. Machine learning are typically classified into three categories: supervised, unsupervised, and reinforcement learning. In some embodiments, supervised machine learning includes support vector machines, linear regression, logistic regression, naive Bayes, linear discriminant analysis, decision trees, k-nearest neighbor algorithm, and similarity learning. Existing unsupervised machine learning methods generally have four different categories: Clustering analysis, sample specificity learning, self-supervised learning, and Generative models. In other embodiments, unsupervised machine learning methods include hierarchical clustering, k-means clustering, density based scan clustering, Gaussian clustering model.

The term "deep learning" as used herein refers to a subset of machine learning based on artificial neural networks model. A well-designed and well-trained deep learning model can perform various tasks classification tasks with higher accuracy and better performance. In some embodiments, supervised deep learning includes deep neural network, recurrent neural networks, convolutional deep neural networks, and their variations. In other embodiments, unsupervised deep learning includes Autoencoders, Deep Belief Nets, Hebbian Learning, Generative adversarial networks (GUNS), and Self-organizing map and their variations.

MRI System Overview

FIG. 1 depicts an MRI system 10, according to one or more embodiments described and shown herewith. In embodiments, the MRI system 10 shown in FIG. 1 includes a patient table 11, a static magnetic field generating unit 12, a gradient magnetic field generating unit 14 for generating respective magnetic fields in proximity to a target area 18 of an object 9, a transmitting and receiving unit 16, and a computing device 100. The patient table 11, the static magnetic field generating unit 12, the gradient magnetic field generating unit 14, and the transmitting and receiving unit 16 are placed within MRI RF shielding area 2 where noise of radio frequency is prevented from entering.

The static magnetic field generating unit 12 includes a main magnet configured to generate a strong static magnetic field in proximity to the target area 18 of the object 9. The static magnetic field generating unit 12 may be arranged to surround the target area 18 of the object 9. For example, the static magnetic field generating unit 12 may be a cylindrical-shaped unit. The gradient magnetic field generating unit 14 includes gradient magnetic field coils for generating gradient magnetic fields in an x-axis direction, a y-axis direction, and a z-axis direction, which are orthogonal to each other. The gradient magnetic field generating unit 14 may be arranged to surround the target area 18 of the object 9. For example, the gradient magnetic field generating unit 14 may be a cylindrical-shaped unit.

In embodiments, the transmitting and receiving unit 16 may include a transmission coil and a receiving coil. The transmission coil irradiates RF pulses to the object 9 and the receiving coil receives MR signals generated by the object 9. In some embodiments, the transmitting and receiving unit 16 may include a transceiver coil having the functions of both the transmission coil and the receiving coil. The receiving coil may be composed of, for example, a so-called array coil in which, for example, a plurality of coil elements are disposed to detect the MR signals generated by the object 9. An RF transmitter 34 may control the transmission coil of the transmitting and receiving unit 16 to irradiate RF pulses. A receiver 40 may receive MR signals generated by the object 9 from the receiving coil of the transmission and receiving unit 16. The RF transmitter 34 and the receiver 40 may communicate with the transmitting and receiving unit 16 through a transmitter/receiver interface 36.

In embodiments, the MRI system 10 includes the computing device 100. The computing device 100 includes a MRI system controller 22. The MRI system controller 22 may control the operations of the gradient coil drivers 32 that activate the gradient coils of the gradient magnetic field generating unit 14. The MRI system controller 22 may also control the operations of the RF transmitter 34 that activates the RF coil of the static magnetic field generating unit 12. The computing device 100 may receive MR signals from the receiving coil of the transmission and receiving unit 16 and reconstruct an MRI image based on the received MR signals. The details of the computing device 100 will be further described with reference to FIG. 1A below.

In embodiment, the computing device 100 may be operably coupled to other components of the MRI system 10, for example, using by any medium that facilitates data exchange between the components of the MRI system 10 and the computing device 100 including, but not limited to, wired, wireless and optical links. For example, the computing device 100 may convert the MR signals received from the transmitting and receiving unit 16 into k-space data. The computing device 100 may generate MR image data from the k-space data with image reconstruction processing. In some embodiments, the techniques for improving image quality with optimal variable flip angles may optionally be implemented using the MRI system 10.

Example Computing Device

Figure 1A:
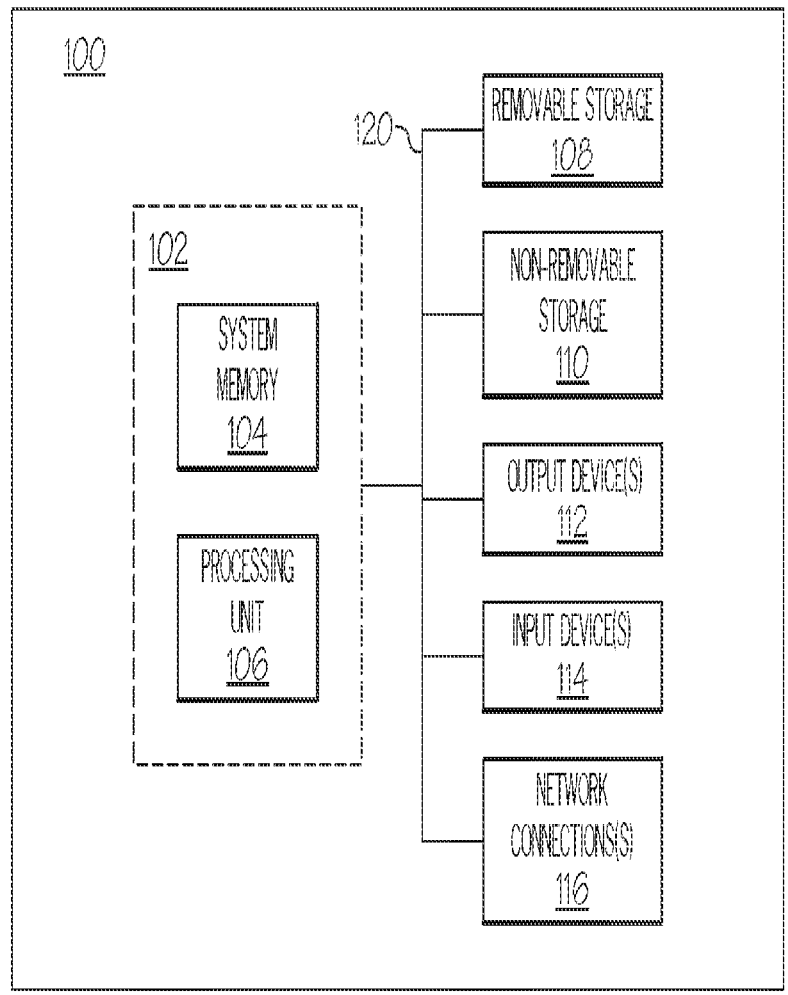
FIG. 1A is an example computing device, according to one or more embodiments shown and described herein.

FIG. 1A depicts a computing device 100 according to one or more embodiments shown and described herein. It should be appreciated that the logical operations described herein with respect to the various figures may be implemented (1) as a sequence of computer implemented acts or program modules (i.e., software) running on a computing device (e.g., the computing device described in FIG. 1A), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

It should be understood that the computing device 100 is only one example of a suitable computing environment upon which embodiments of the invention may be implemented. Optionally, the computing device 100 may be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In embodiments, the computing device 100 includes a controller 102 that includes one or more processing units 106 and one or more system memory modules 104. The controller 102 may be the same controller as the MRI system controller 22 in FIG. 1. In other embodiments, the controller 102 may be a separate controller from the MRI system controller 22 in FIG. 1.

Depending on the exact configuration and type of computing device, the one or more memory modules 104 may be volatile (such as random access memory (RAM)), non-volatile (such as read-only memory (ROM), flash memory, etc.), or some combination of the two. The one or more processing units 106 may be a standard programmable processor that performs arithmetic and logic operations necessary for operation of the computing device 100.

In embodiments, the computing device 100 includes communication path 120 that provides signal interconnectivity between various components of the computing device 100. Accordingly, the communication path 120 may communicatively couple any number of processing units 106 with one another, and allow the components coupled to the communication path 120 to operate in a distributed computing environment. Specifically, each of the components may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 120 may be formed from any medium that is capable of transmitting a signal such as, for example, conductive wires, conductive traces, optical waveguides, or the like. In some embodiments, the communication path 120 may facilitate the transmission of wireless signals, such as Wi-Fi, Bluetooth, Near Field Communication (NFC) and the like. Moreover, the communication path 120 may be formed from a combination of mediums capable of transmitting signals. In one embodiment, the communication path 120 comprises a combination of conductive traces, conductive wires, connectors, and buses that cooperate to permit the transmission of electrical data signals to components such as processors, memories, sensors, input devices, output devices, and communication devices. Accordingly, the communication path 120 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The one or more processing units 106 may be configured to execute program code encoded in tangible, computer-readable media. Tangible, computer-readable media refers to any media that is capable of providing data that causes the computing device 100 (i.e., a machine) to operate in a particular fashion. Various computer-readable media may be utilized to provide instructions to the one or more processing units 106 for execution. Example tangible, computer-readable media may include, but is not limited to, volatile media, non-volatile media, removable media and non-removable media implemented in any method or technology for storage of information such as computer readable instructions, data structures, program modules or other data. One or more system memory modules 104, a removable storage 108, and a non-removable storage 110 are all examples of tangible, computer storage media. Tangible, computer-readable recording media may include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In embodiments, the one or more processing units 106 may execute program code stored in the one or more system memory modules 104. For example, a bus may carry data to the one or more system memory modules 104, from which the one or more processing units 106 receive and execute instructions. The data received by the one or more system memory modules 104 may be optionally stored on the removable storage 108 or the non-removable storage 110 before or after execution by the processing unit 106.

In embodiments, the computing device 100 may include additional storage such as removable storage 108 and non-removable storage 110 including, but not limited to, magnetic or optical disks or tapes.

The computing device 100 may also have input device(s) 114 such as a keyboard, mouse, touch screen, etc. The input device may be manipulated by an operator to input signals to the MRI apparatus to set the imaging method group, the performing order, the imaging condition, and the like. The computing device 100 may also have output device(s) 112 such as a display, speakers, printer, etc. The output device 112 may output image data such as local image data, diagnosis image data using display, printer and other displayer. The additional devices may be connected to the bus in order to facilitate communication of data among the components of the computing device 100.

Computing device 100 may also contain network connection(s) 116 that allow the device to communicate with other devices. The network connection(s) 116 may be any device capable of transmitting and/or receiving data via a wireless network. Accordingly, the network connection(s) 116 may include a communication transceiver for sending and/or receiving data according to any wireless communication standard. For example, the network connection(s) 116 may include a chipset (e.g., antenna, processors, machine readable instructions, etc.) to communicate over wireless computer networks such as, for example, wireless fidelity (Wi-Fi), WiMax, Bluetooth, IrDA, Wireless USB, Z-Wave, ZigBee, or the like.

It should be understood that various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

In some embodiments, the computing device 100 may include a workflow setting unit, an imaging operation determining unit, and an image reconstruction unit. The workflow setting unit may be a program module stored in the system memory modules 104. The workflow setting unit sets a first workflow relating to the MRI examination by estimating an imaging time of each of the imaging methods in the performing order initially set by a scan plan. Further, the workflow setting unit sets a second workflow relating to the MRI examination by estimating a shortest performing order, by which an examination time necessary to sequentially perform a plurality of imaging methods constituting the imaging method group set by the input unit is minimized. The imaging operation determining unit determines whether an imaging operation during a main imaging is implemented according to the workflow. In embodiments, the workflow setting unit and/or the imaging operation unit may be implemented using hardware, software, and or a combination thereof.

The image reconstruction unit may include an MR signal storage unit, a signal processing unit, and an image data storage unit. The MR signal storage unit (e.g., memory) stores the MR signals, which are collected by the receiver unit of the transmitting and receiving unit 16. The signal processing unit has an image reconstruction processing unit and an image processing unit. The image reconstruction processing unit generates image data from the MR signal storage unit by image reconstruction processing, for example, performed by a Fourier transformation such as 2D FFT. When the MR signals to a three-dimensional region are collected, the image reconstruction processing unit of the signal processing unit generates volume data. Subsequently, the image processing unit generates three-dimensional image data such as volume rendering image data, surface rendering image data and the like or two-dimensional image data, multi planar reconstruction image data, and the like, because predetermined image processing is performed for the volume data generated by the image reconstruction processing unit. Then, the image data described above obtained by the signal processing unit are stored to the respective storage regions of the image data storage unit.

Intra-Tumor Heterogeneity Overview

There are more than 18 million cancer cases and over 8 million people die of cancer around the world each year. Despite tremendous efforts to cancer therapy over the past decades, overall cancer mortality remains high and has not changed substantially. The cancer therapy is mainly challenged by spatiotemporal intra-tumor and inter-tumor heterogeneity in genetic and molecular levels. A tumor consists of billions of independent cancer cells. Specifically, the tumor is complicated by spatiotemporal heterogeneity of cell types, including malignant, immune, and stromal cells. The DNA damage or changes in microenvironment introduced at each cell division may cause slight changes of cancer cell genome. The natural consequence of this evolutionary process leads to the diversity or heterogeneity of cancer cells within the same tumor at genetic and molecular level, known as intra-tumor heterogeneity. For example, the cell diversity or heterogeneity across patients, inter-site tumors, and intra-site tumor, results in the incurable glioblastoma. The intra-tumor heterogeneity has three major influences on the understanding of cancer mechanism, diagnosis and prognosis of the cancer.

First, single cell genomic profiling is a powerful new tool for investigating evolution and diversity in cancer and understanding the role of rare cells in tumor progression. Clonal diversity is destined to play an important role in invasion, metastasis, and the evolution of resistance to therapy.

Second, in the current era of precision medicine, targeted cancer treatment is carried out according to the molecular or genomic characterization of the cancer the individual has, because each cancer with the different molecular or genomic phenotype underlie the differences in treatment responses. For example, identification of HER2+ subtype of breast cancer brain metastases is critical for targeted therapies and potentially improve survival outcomes for patients. The identification of tumor evolution is very important in the design of targeted therapeutic strategies as it guides the selection of the most appropriate drug combinations according to the molecular or genomic characterization of the cancer. That is, the identification of driver mutations in a cancer as therapeutic targets is very critical for precision medicine in cancer.

Finally, successive cancer therapies may arise the variations in gene expression and mutations that may confer drug resistance or susceptibility. It is clear that a heterogeneous tumor with many different genetic or molecular profiles may be more likely than a homogeneous tumor leads to treatment failure or relapse. The real-time identification of ongoing intra-tumor heterogeneity during therapy may adjust the timely treatment strategies, greatly improve the management of cancer patients, reduce the cost of healthcare, and then improve the outcome of cancer patients.

In conclusion, it is well known that intra-tumor heterogeneity is strongly associated with the understanding of cancer mechanism, genetic or molecular diagnosis, targeted therapy, therapeutic resistance and poor patient outcomes in many different tumor types. However, identification of the intra-tumor heterogeneity is still a major challenge. Therefore, there is an urgent requirement for not only precision medicine, but also for preclinical and pharmaceutical research to detect and characterize intra-tumor heterogeneity at genetic or molecular level in fast, accurate and non-invasive procedure.

To date, intra-tumor heterogeneity has been explored using two major class methods: multi-regional DNA or RNA sequence method and image biomarker-based methods.

The first class methods are to perform multi-regional DNA or RNA sequence analysis of surgical specimens. The methods are a gold standard to validate the measurement of intra-tumor heterogeneity. However, measurement of intra-tumor heterogeneity by either surgical biopsy or liquid biopsy was a very long process that caused unwanted changes to the cellular genetic profile, particularly for very aggressive tumor, such as glioma and brain metastases. Additionally, these methods are completely impractical for real-time identifying intra-tumor heterogeneity for diagnosis, treatment assessment and outcome prediction. For example, imaging systems are unable to detect detailed cellular signaling and biological processes within the tumor, and multiple biopsies through the treatment would be too invasive. Most recently, a lot of studies indicate the existence of intra-site tumor heterogeneity. For example, multiregional sequencing of renal carcinoma, glioblastoma, and lung cancer have all showed significant divergence between distinct areas of the same tumor.

Histopathology is the most reliable "gold standard" method for identify intra-site tumor heterogeneity of cancers because histopathological exams have very high spatial resolution. However, surgical biopsy and liquid biopsy have certain limitations: First it is an invasive procedure and is sometimes not feasible in eloquent areas or difficult to access locations. For example, it is very risky and challenging to perform repeat surgical biopsy in brain. Second, tissue and liquid biopsy may not fully reflect the overall picture of the tumor, due to its heterogeneity. Particularly in the early stage of treatment, mixed morphology consisting of both treatment effects and cancer emphasize limit the accuracy of surgery biopsy. It is sensitive to inherent sampling error. Third, histological examinations are extensive and costly. The procedure for histological examinations is time-consuming and labor-intensive. For example, conventional detection and treatment assessment of cancer or tumor can be performed by estimating changes in the number of cancer cells with tissue biopsy or a liquid biopsy. The biopsy procedure is invasive, as molecular or genetic subtypes must be extracted from biopsy tissue. A routine biopsy examination takes 3 to 7 days. There are also the added expenses of labor and equipment to perform the biopsy. Four, histological exams is an operator-dependent. It has a variability cross individual operator. Five, it is impossible for histological examinations to perform in vivo non-invasive monitoring of the tissue changes. Six, liquid biopsy is limited by three major factors: (a) the molecules obtained from the liquid biopsy may be made by both molecular or genetic subtypes; (b) the quantities of molecules obtained from liquid biopsy is too small to detect; (c) liquid biopsy is impossible to identify the intra-site tumor heterogeneity. Finally, the biopsy is a complicated procedure, and not all patients may agree to undergo it. Therefore, there is still challenge to identify the intra-tumor heterogeneity using surgical biopsy or liquid biopsy, more specially to identify the intra-site tumor heterogeneity.

In order to overcome the drawbacks of the first class methods, the second class methods are to identify the genetic or molecular profiles using the quantitative image biomarkers derived from radiological images. The radiological images provide a means of noninvasive sampling of tumor microenvironments, allowing for a dynamic and comprehensive evaluation of regional intra-tumor heterogeneity of cancer cells or molecules. The imaging methods have the following advantages: (1) The imaging methods can provide a non-invasive, cheap, repeated and fully covered treatment assessment. (2) The imaging methods allow information to be obtained about the tissues within a few minutes. It is possible to develop a real-time method to provide information on a tumor's overall shape, growth over time, and heterogeneity, making it an attractive and favored biopsy alternative. However, the conventional imaging methods is still challenged for identifying intra-site tumor heterogeneity because the spatial and temporal resolution of current brain tumor imaging is relatively low. Specifically, detectable tumor size is more than 3 voxel. The imaging methods require quantifying the image feature, particularly high-order features. In addition, several unresolved issues such as late detection, failure to recognize the genetic and molecular heterogeneity of tumors, drug resistance, etc. clearly necessitate development of new approaches to improve the efficacy of cancer therapy.

Figure 2:
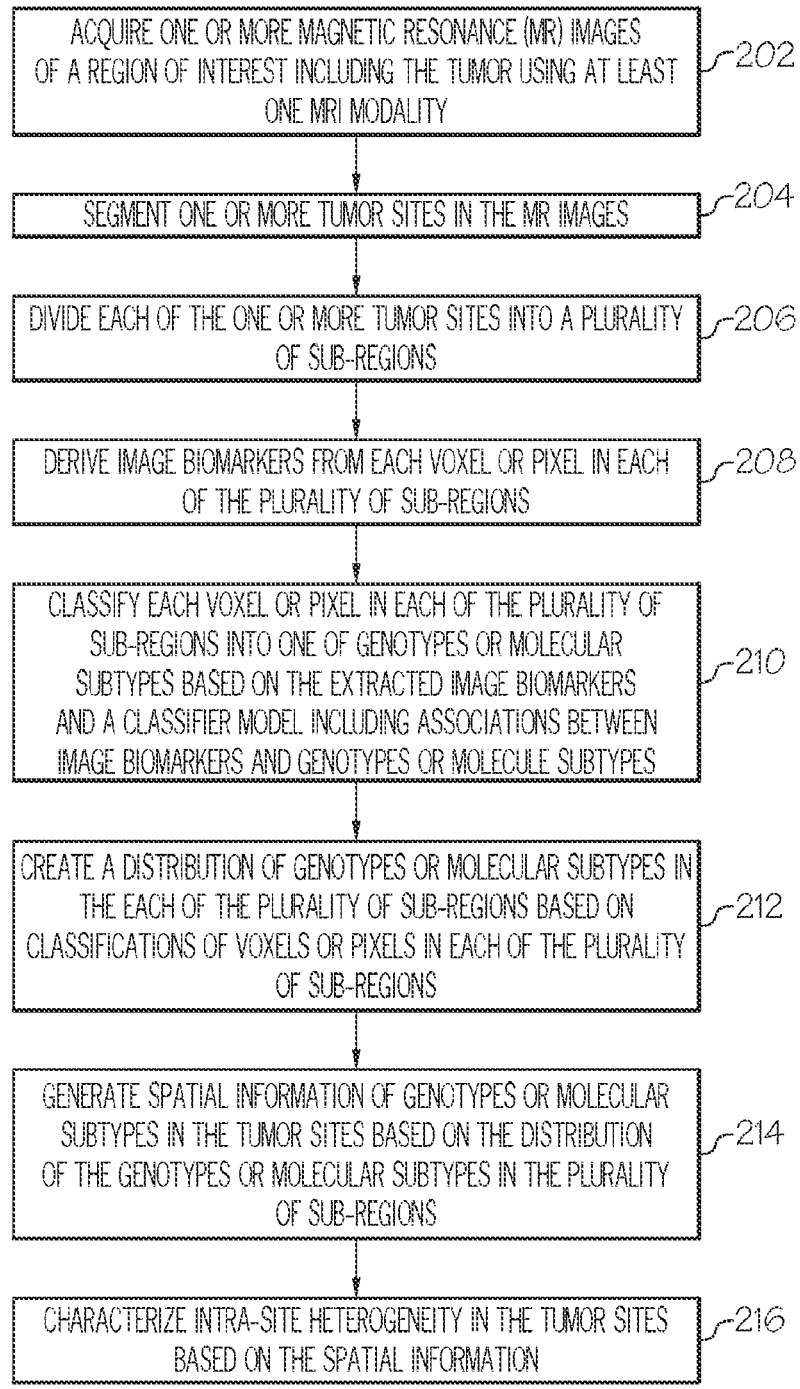
FIG. 2 is a flowchart illustrating example operations for characterizing intra-site tumor heterogeneity.

The present disclosure provides a method to identify intra-site tumor heterogeneity using quantitative imaging biomarkers. FIG. 2 shows a flowchart illustrating example operations for measuring intra-site tumor heterogeneity in a brain tumor site using magnetic resonance imaging.

In step 202, the MRI system 10 acquires one or more magnetic resonance (MR) images of a region of interest including the tumor using at least one MRI modality.

In embodiments, the MR images may be acquired using at least one of the magnetic resonance imaging (MRI) modalities consisting of T1-weighted imaging, T2-weighted imaging, diffusion-weighted imaging, functional MR imaging, diffusion tensor imaging, susceptibility-weighted imaging, perfusion-weighted imaging, chemical shift imaging, and intra-voxel incoherent motion, and their variations. In embodiments, the MR images may be obtained with or without administering contrast agent to the subject. For example, the MR images may be obtained by contrast enhanced imaging sequence. An exogenous or endogenous tracer may be administered into the subject before acquiring the MR images. In some embodiments, the MRI system 10 may pre-process the acquired MR images. The pre-processing may include one or more of motion correction, voxel/pixel resampling, filtering, artifact reduction, harmonization, signal normalization and image co-registration.

In step 204, the MRI system 10 segments one or more tumor sites in the MR images.

In step 206, the MRI system 10 divides each of the one or more tumor sites into a plurality of sub-regions.

In step 208, the MRI system 10 derives image biomarkers from each voxel or pixel in each of the plurality of sub-regions.

In step 210, the MRI system 10 classifies each voxel or pixel in each of the plurality of sub-regions into one of genotypes or molecular subtypes based on the extracted image biomarkers and a classifier model including associations between image biomarkers and genotypes or molecule subtypes. In embodiments, the MRI system 10 classifies individual pixels or voxels into molecular or genetic subtypes, such as HER2+ subtype breast cancer brain metastases, IDH-wild subtype Glioblastoma Multiforme, and IDH-mutant subtype Glioblastoma Multiform. In embodiments, the classifier model may be an unsupervised classification model, such as a multiple clustering model. In some embodiments, the classifier model may be a supervised classification including at least one of a fuzzy logic algorithm, a support vector machine algorithm, a regression random forest, a Gaussian mixture model, a machine learning algorithm, a deep learning algorithm. In some embodiments, the classifier model may be a biophysical model or biomarker to differentiate cell subtypes. The details of classifying cells will be further explained below with reference to FIG. 5.

Figure 7A:
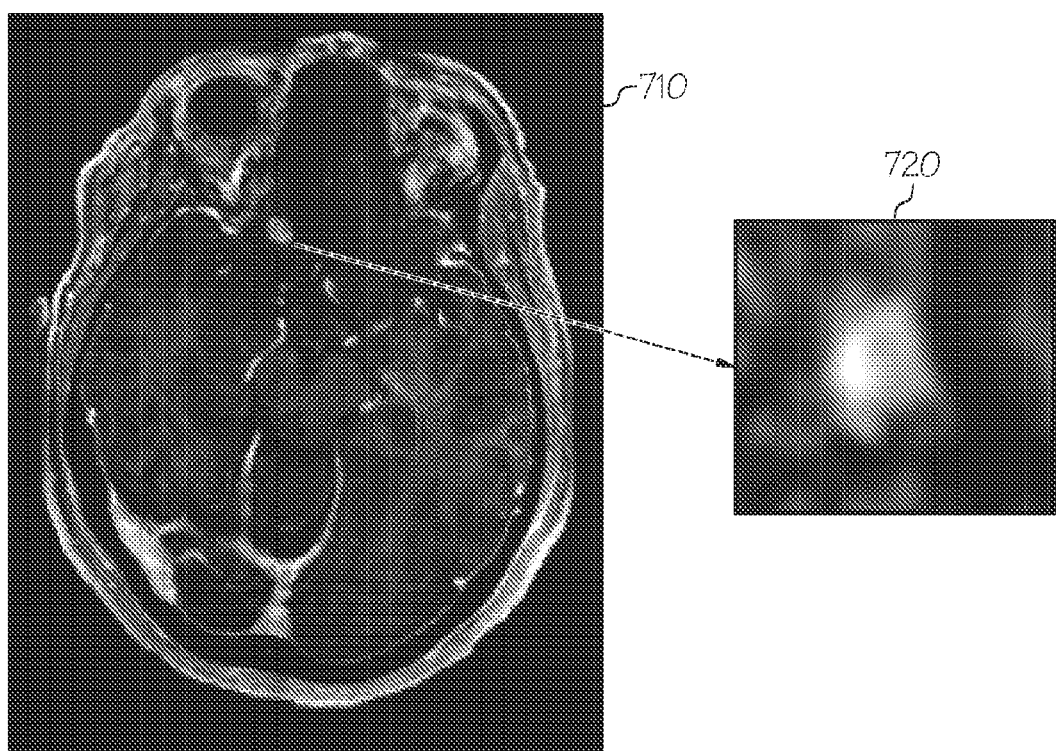
FIG. 7A depicts a multi-modal MRI image.
Figure 7B:
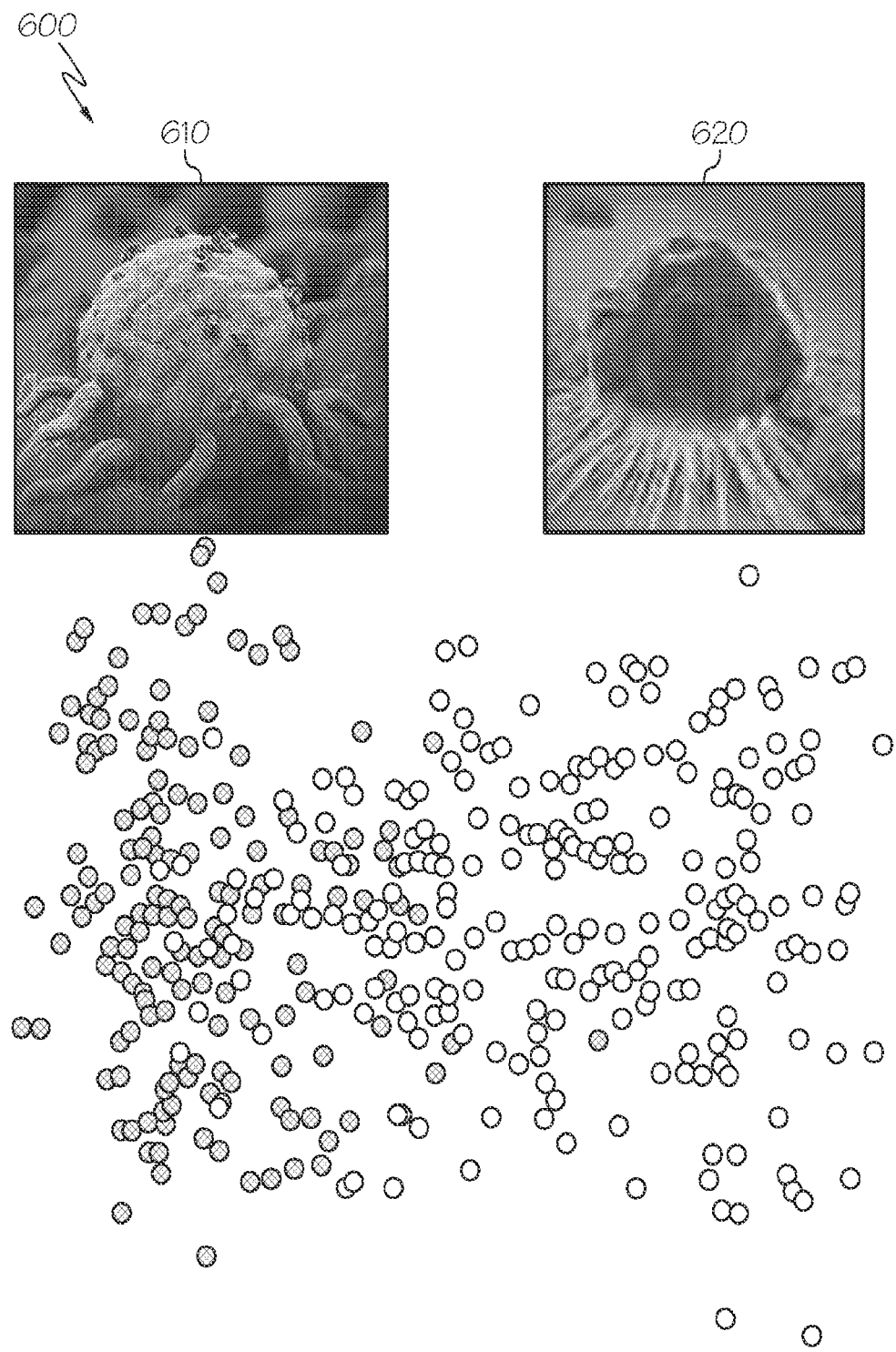
FIG. 7B depicts an example of classifying molecular or genetic subtypes into two classes using unsupervised machine learning methods based on the inputted radiological image.
Figure 7C:
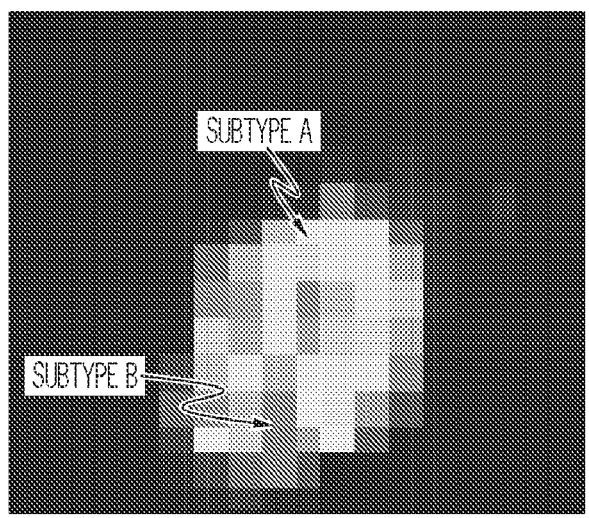
FIG. 7C illustrates a distribution of two different genetic types, genetic type A and a genetic type B, in a sub-region.

In step 212, the MRI system 10 creates a distribution of genotypes or molecular subtypes in the each of the plurality of sub-regions based on classifications of voxels or pixels in each of the plurality of sub-regions. For example, FIG. 7C illustrates a distribution of two different genetic types, genetic type A and a genetic type B, in a sub-region.

In step 214, the MRI system 10 generates spatial information of genotypes or molecular subtypes in the tumor sites based on the distribution of the genotypes or molecular subtypes in the plurality of sub-regions.

In step 216, the MRI system 10 characterizes intra-site heterogeneity in the tumor sites based on the spatial information.

The method according to the present disclosure applies non-invasive medical imaging for the identification of intra-site tumor heterogeneity in brain tumors. Compared with the existence of conventional non-invasive imaging method for identify the intra-tumor heterogeneity, the present method provides following technical benefits.

First, most conventional non-invasive imaging methods base on relatively low spatial resolution images which lead to the big error in the quantification of radiomic features because radiomic features are sensitive to the imaging acquisition parameters (such as spatial resolution). The spatial resolution of MRI protocols recommended by FDA and NCI of not less than 1.0 mm is not sufficient to accurately evaluate intra-site tumor heterogeneity of brain tumor, more particularly small brain tumor (<5 mm), The progression of these techniques provides a potential to characterize the cancer biology properties inside a cancer using high resolution images, particularly when the cancer size is comparable to the voxel size of the images. In the present disclosure, MRI images with high spatial resolution are acquired to identify the intra-site tumor heterogeneity. In the present disclosure, the spatial resolution may be less than 1.0 mm.

Second, most conventional non-invasive imaging methods target the measurable tumor size of more than 5.0 mm. In contrast, the present disclosure targets the measurable tumor size of less than 5.0 mm. For example, the present disclosure may target the small measurable tumor size which is around 8 folds of voxel numbers. That is, for the image spatial resolution of 1.0 mm, the measurable tumor size may be around 2.0 mm.

Third, feature selection is very important for avoiding overfitting of the classifier models to identify the intra-site tumor heterogeneity. In the present disclosure, only stable and robust radiomic features associated with cancer biology are selected to identify the intra-site tumor heterogeneity, especially the number of available datasets is often limited.

Fourth, the image biomarkers or radiomic features of a voxel or pixel are estimated from the nearest or secondary nearest voxels or pixels of the voxel or pixel within a tumor site in the present invention, in contrast with conventional technologies where the radiomic features are estimated from entire tumor in the individual site.

Finally, the present disclosure about intra-site tumor heterogeneity may lead to distinct treatment strategies. The conventional technologies assume that each tumor site is homogeneous and ignore the intra-site tumor heterogeneity. As a result, a tumor with intra-site tumor heterogeneity is only targeted to one of molecule profiles. For example, patients with HER2+ breast cancer brain metastases may be treated by anti-cancer drugs, including Lapatinib-capecitabine, Trastuzumab-Doxil, Trastuzumab-carboplatin. However, the present method may identify intra-site tumor heterogeneity more accurately and timely. For example, patients with HER2+ and triple negative breast cancer brain metastases may be treated by mixed anti-cancer drug or systematic immunotherapy for targeting both molecular phenotypes.

Despite substantial challenges, targeted clinical implementation of AI methods in neuro-oncology is set to transform the field into an era of precision medicine. Most applications of machine learning in medical imaging have relied on supervised forms of machine learning, which consist of algorithms that are trained on "ground truth" labels. Labels may include one or more tumor with different genetic and molecular types that are obtained from histopathological examination of tissue samples collected during tumor resection or biopsy. For example, artificial intelligence models based on image features and clinical data may be used to identify specific gene mutations from tumor pathology images instead of using traditional genomic sequencing, predict outcome for patients with various diseases, and evaluate the effectiveness of therapies.

Figure 3A:
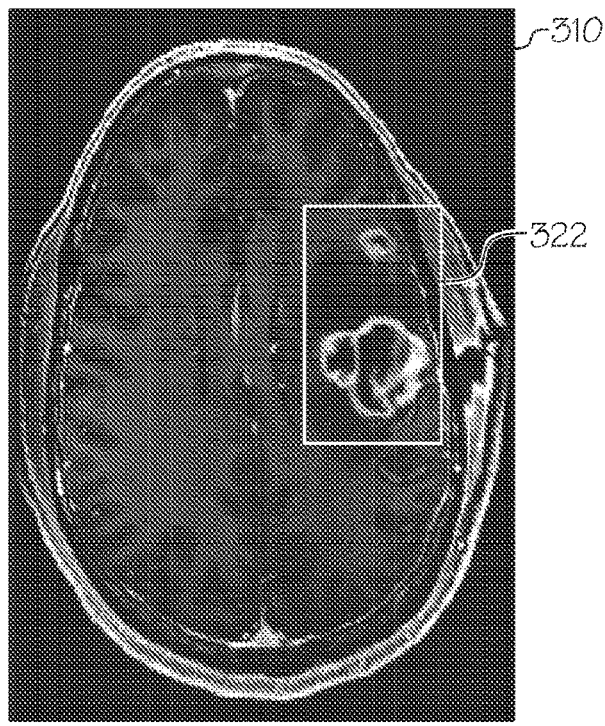
FIG. 3A illustrates an exemplary glioblastoma multiforme brain image with a spatial resolution of 1.0 mm.
Figure 3B:
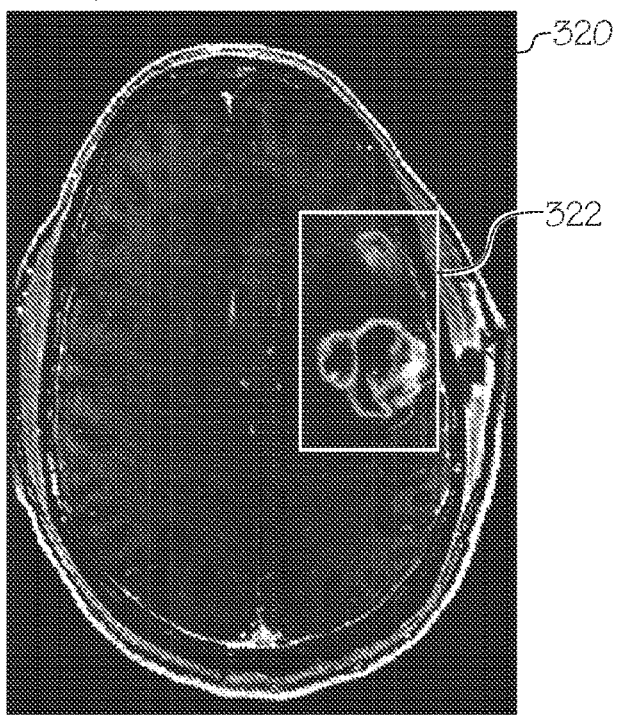
FIG. 3B illustrates an exemplary glioblastoma multiforme brain image with a spatial resolution of 0.7 mm.

FIGS. 3A and 3B depict example glioblastoma multiforme brain images 310 and 320 with different isotropic spatial resolution of 1.0 mm and 0.7 mm. The images 310 and 320 include regions of interest 312 and 322, respectively. The images with higher spatial resolution shows better tumor-tissue contrast, sharper tumor-tissue boundary, and better definition of the tumor architecture which is pre-requisite to identify intra-site tumor heterogeneity. For example, the image for the region of interest 322 obtained with the spatial resolution of 0.7 mm shows better tumor-tissue contrast, sharper tumor-tissue boundary, and better definition of the tumor architecture than the image for the region of interest 312 obtained with the spatial resolution of 1.0 mm. At the lower spatial resolution, the whole tumor site may be approximated to be homogeneous. For example, the whole tumor site in the image for the region of interest 312 may be approximated to be homogenous. As a result, it is very difficult or impossible to identify the intra-site tumor molecular or genetic heterogeneity from these radiological images. The present disclosure bases on the assumption that some of molecular or genetic subtypes of tumor associate with the image features.

Figure 4A:
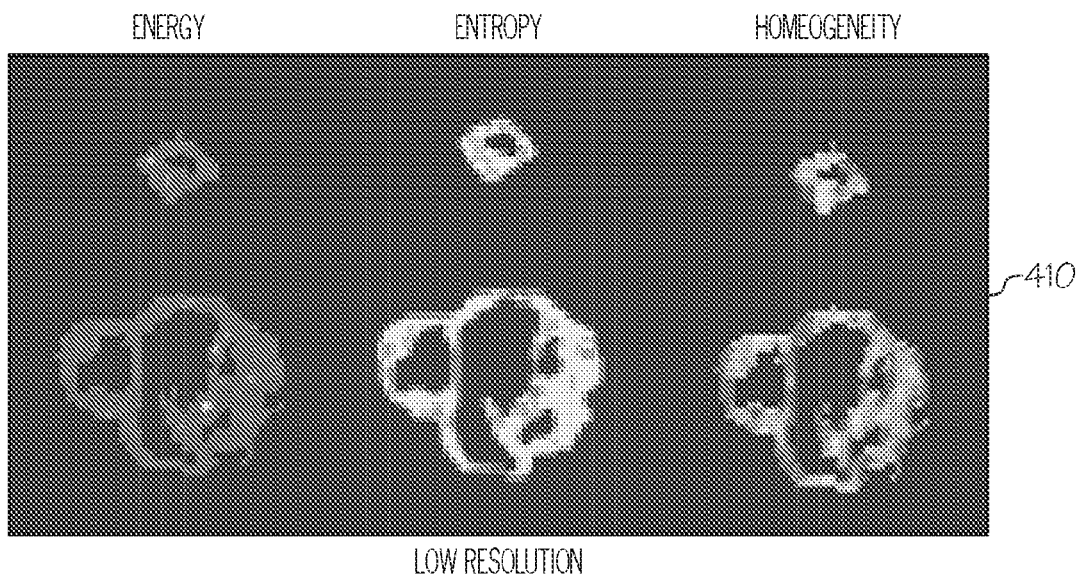
FIG. 4A illustrates exemplary radiomic features for an image having a spatial resolution of 1.0 mm.
Figure 4B:
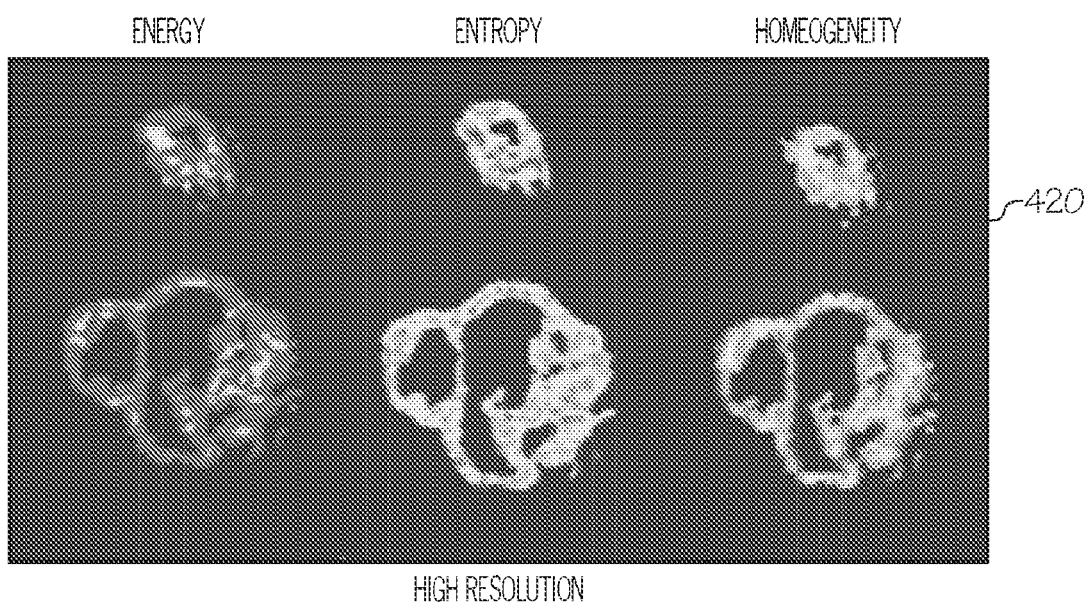
FIG. 4B illustrates exemplary radiomic features for an image having a spatial resolution of 0.7 mm.

FIGS. 4A and 4B depict an example how different spatial resolutions influence quantitative radiomic features. An image 410 in FIG. 4A depicts radiomic features of a region of interest 312 in FIG. 3A including energy, entropy, and homogeneity of the region of interest. The image 410 is obtained with the spatial resolution of 1.0 mm. Similarly, an image 420 in FIG. 4B depicts radiomic features of a region of interest 322 in FIG. 3B including energy, entropy, and homogeneity of the region of interest. The image 420 is obtained with the spatial resolution of 0.7 mm. Generally, the images with higher spatial resolution may provide more accuracy of quantitative radiomic features because most radiomic features are estimated by first-, second-, and higher-order statistics of radiological images. For example, the image 420 with the spatial resolution of 0.7 mm provides more accurate quantitative radiomic features than the image 410 with the spatial resolution of 1.0 mm. The more pixels or voxels present in tumor, the more accurate statistic results. In some embodiments, various radiomic features can be extracted from MR images. The radiomic features may include, but are not limited to, size and shape based— features, descriptors of the image intensity histogram, descriptors of the relationships between image voxels (e.g., gray-level co-occurrence matrix, run length matrix, size zone matrix, and neighborhood gray tone difference matrix derived textures), and textures extracted from filtered images, and fractal features.

Figure 5:
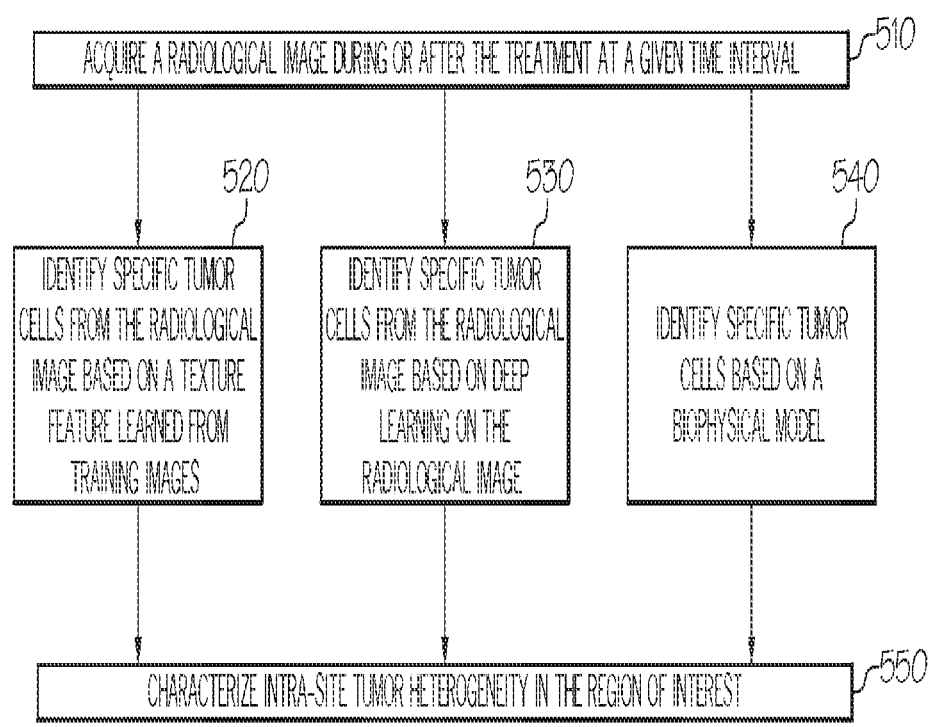
FIG. 5 is an example flowchart of identifying intra-site tumor heterogeneity

FIG. 5 depicts a flowchart for characterizing intra-site tumor heterogeneity according to one or more embodiments shown and described herein.

In step 510, the MRI system 10 acquires a radiological image during or after the treatment. Once the radiological image is acquired, the MRI system identifies specific molecular or genetic subtypes in the radiological image using various methods, for example, three different methods described in steps 520, 530, 540.

As one of the methods for identifying the specific molecular or genetic subtypes, in step 520, the MRI system 10 may identify specific molecular or genetic subtypes from the radiological image based on a texture learned from training images. For example, the texture may be learned based on machine learning on images that include features for the specific molecular or genetic subtypes. The details of the machine learning will be described below with reference to FIGS. 6, 7A-C.

As another method for identifying the specific molecular or genetic subtypes, in step 530, the MRI system 10 may identify specific molecular or genetic subtypes from the radiological image based on deep learning on the radiological image. The details of the machine learning will be described below with reference to FIGS. 8-10.

As another method for identifying the specific molecular or genetic subtypes, in step 540, the MRI system 10 may identify specific tumor cells from the radiological image based on application of a biophysical model on the radiological image. The biophysical model may be a simulation of a biological system using mathematical formalizations of the physical properties of that system. Such models can be used to predict the influence of biological and physical factors on complex systems. For example, the uncontrolled division of cells in a tumor region requires acquisition of necessary nutrients from a frequently nutrient-poor environment, leading to increased blood volume. As a result, dynamic susceptibility contrast MRI indicates measures of cerebral blood volume are significantly higher in a tumor region compared with a non-tumor region. Thus, the cerebral blood volume may be a marker to identify the molecular or genetic subtypes.

The objective of these methods in steps 520, 530, 540 is to uncover the relationship between image features and molecular or genetic subtypes by mathematical or statistical models in order to identify intra-site tumor heterogeneity over time during or after anti-cancer therapy.

In step 550, the MRI system 10 may characterize intra-site tumor heterogeneity in the region of interest based on the identification of specific molecular or genetic subtypes in steps 520, 530, or 540. The MRI system 10 may create a distribution of genotypes or molecular subtypes in the each of the plurality of sub-regions based on classifications of voxels or pixels in each of the plurality of sub-regions based on the identified intra-site tumor heterogeneity.

In embodiments, a support vector machine with radiomic features may be employed to predict recovery outcome in patients with Intracerebral hemorrhage (ICH). The following schema for fluid-attenuated inversion recovery (FLAIR) MRI data preprocessing may be conducted: 1) skull stripping (comprises the process of removing skull, extra-meningeal and non-brain tissues from the MRI data); 2) bias field correction (removing the signal intensity inhomogeneity mainly caused by radiofrequency coils); and 3) intensity normalization (reducing the variations of signal intensity and contrast across subjects). After the preprocessing, 3D U-Net convolutional neural network model may be implemented to segment hemorrhages. Then, 105 radiomics features from the segmented hemorrhages may be extracted using pyRadiomics pipeline, including 13 geometric features (e.g., volume, surface area, compactness, maximum diameter, sphericity), 18 histogram features (e.g., variance, skewness, kurtosis, uniformity, entropy), 14 texture features from the Gray-Level Dependence Matrix, 23 texture features from the Gray-Level Co-Occurrence Matrix, 16 texture features from the Gray-Level Run-Length Matrix, 16 texture features from the Gray-Level Size Zone Matrix, and 5 texture features from the Neighborhood Gray-Tone Difference Matrix. To prevent model overfitting, feature dimensionality using least absolute shrinkage and selection operator (LASSO) algorithm may be reduced. The LASSO algorithm minimizes the residual sum of squares and poses a constraint to the sum of the absolute values of the coefficients being less than a constant. The LASSO algorithm constructs a linear model, which penalizes the coefficients with an L1 penalty, such that some coefficients can be shrunk to zero. Features with non-zero coefficients were selected by the LASSO. Based on the 54 LASSO-selected radiomics features, a support vector machine (SVM) model with a polynomial kernel to conduct two-class classification is generated. Using a 5-fold cross-validation, the classification diagnostic performance of our SVM models may be established, including accuracy, sensitivity, specificity, and area under the receiver operating characteristic curve. As a result, the present method can correctly identify patients likely to have unfavorable outcomes with an accuracy of 80.8% (95% confidence interval: 78.9%, 82.8%), AUC of 0.81 (95% confidence interval: 0.79, 0.83), sensitivity of 88.2% (95% confidence interval: 86.1%, 90.4%) and specificity of 72.7% (95% confidence interval: 69.0%, 76.4%).

Figure 6:
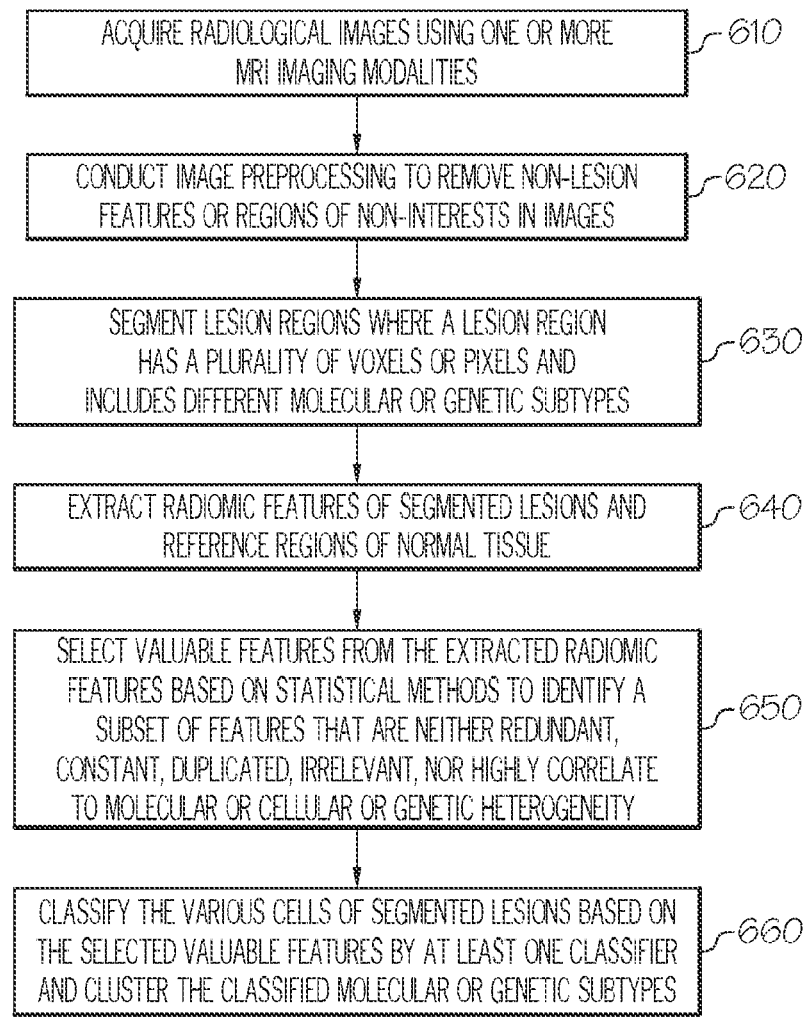
FIG. 6 is an example operation for identifying intra-tumor heterogeneity using a machine learning classifier model with radiological image features.

FIG. 6 depicts a flowchart for classifying and clustering tumor heterogeneity at the molecular and genetic levels by integrating image features and machine learning algorithms according to one or more embodiments shown and described herein. In step 610, the MRI system 10 acquires radiological images using one or more MRI imaging modalities, such as T1-weighted imaging, T2-weighted imaging, diffusion-weighted imaging, functional MR imaging, diffusion tensor imaging, susceptibility-weighted imaging, perfusion-weighted imaging, chemical shift imaging, and intra-voxel incoherent motion, and their variations. For example, the MRI system 10 acquires a multi-modal MRI image 710 (Post-T1-weighted image) in FIG. 7A. As illustrated in FIG. 7A, the image 710 may include a segmented region 720 that includes cancer cells.

In step 620, the MRI system 10 conducts image preprocessing to remove non-lesion features or regions of non-interests in images.

In step 630, the MRI system 10 segments lesion regions (e.g. tumor, edema, necrosis, etc.) where a lesion region has a plurality of voxels or pixels and includes tumor cells, inflammation cells, and normal tissue cells.

In step 640, the MRI system 10 extracts radiomic features of the segmented lesion regions and reference regions of normal tissue. The various methods, such as PyRadiomics, MaZda, LifeX, and Z-Rad, may be used to extract the radiomic features, where the features include, but are not limited to, size and shape based—features, descriptors of the image intensity histogram, descriptors of the relationships between image voxels (e.g., gray-level co-occurrence matrix, run length matrix, size zone matrix, and neighborhood gray tone difference matrix derived textures), and textures extracted from filtered images, and fractal features. A large number of extracted features may be used to distinguishing the parameters relevant to molecular or cellular or genetic heterogeneity.

In step 650, the MRI system 10 selects valuable features from the extracted radiomic features based on statistical methods to identify a subset of features that are neither redundant, constant, duplicated, irrelevant, nor highly correlate to molecular or cellular or genetic heterogeneity. At least one feature extracted from the segmented lesion regions may represent features related to molecular or genetic subtypes and/or gene mutations. Additionally, at least one feature extracted from reference regions may correspond to features related to normal tissue cells. For example, the features of molecular or genetic subtypes correspond to high entropy, compared with the features of normal tissue cells.

In step 660, the MRI system 10 classifies the various cells of segmented lesion regions based on the selected valuable features by at least one classifier and clusters the classified cells. For example, FIG. 7B depicts an example of classifying tumor cells into two molecular or genetic subtypes using unsupervised machine learning methods based on the inputted radiological image 600. The MRI system 10 may classify the group of cells 600 into either molecular or genetic subtypes of genetic type A 610 or molecular or genetic types of genetic type B 620. Then, the MRI system 10 may cluster tumor cells based on the classified molecular or genetic subtypes. For example, by referring to FIG. 7C, the MRI system 10 may cluster tumor cells having the molecular or genetic subtypes of genetic type A and cluster cells having the molecular or genetic types of genetic type B such that a distribution of clusters of different molecular or genetic types may be illustrated. Specifically, clustered tumor cells having the molecular or genetic subtypes of genetic type A is illustrated in green, and clustered tumor cells having molecular or genetic subtypes of genetic type B is illustrated in red. That is, FIG. 7C is an example of output for intra-site tumor heterogeneity.

Traditional machine learning requires explicit feature extraction to reduce data complexity. Such approaches are often less adequate in properly modeling high-dimensional data. Alternatively, deep learning enables the extraction of biologically meaningful features and revealing discriminative information from complex and high-dimensional data automatically via self-learning. Unsupervised tools are likely the best candidates to explore intra-site tumor heterogeneity because of the following reasons: (1) Image associated with the complicate heterogeneity (i.e. genetic, epi-genetic, environment); (2) only relatively small labeled samples that can be used to contacting genetic and molecular profiles with image features; (3) potential bias of the labeled samples. In some embodiments, the classifier is an unsupervised clustering algorithm/model, which can identify multiple cell types with or without genetic heterogeneity in high dimensional image feature space. In some embodiments, the classifier is a supervised classification algorithm/model, which is trained on a set of image features derived from acquired high resolution images of preselected patient populations or simulated images with the specific molecular or genetic subtypes. The trained model is fine-tuned and validated on a separate independent set of images. Finally, another independent set of images is used to test the model and report final statistical results. It is noted that each of the three sets of images should be independent, without overlap. Also, the inclusion and exclusion criteria for the dataset, in addition to the justification for removing any outlier, should be explained.

Figure 8:
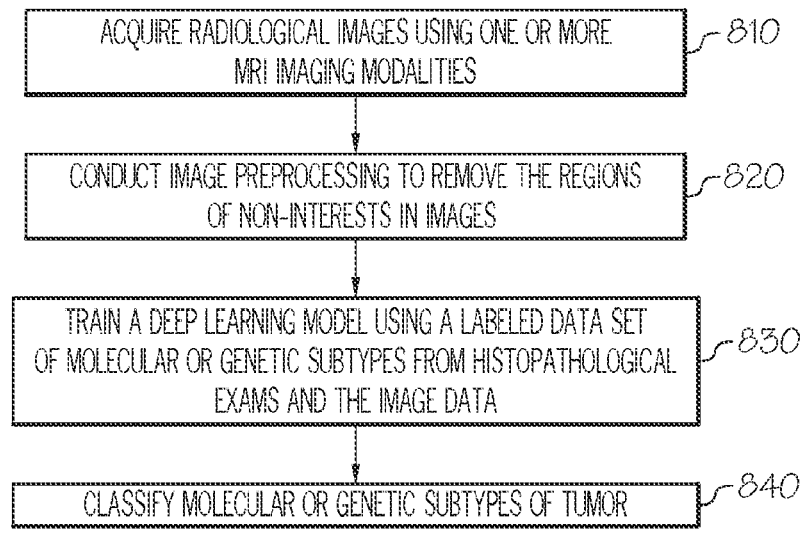
FIG. 8 is an example operation for classifying and quantifying molecular or genetic types by a deep learning model.

FIG. 8 depicts a flowchart for classifying molecular or genetic subtypes by a deep learning model and identifying intra-site tumor heterogeneity according to one or more embodiments shown and described herewith.

In step 810, the MRI system 10 acquires radiological images using one or more MRI imaging modalities, such as T1-weighted imaging, T2-weighted imaging, diffusion-weighted imaging, functional MR imaging, diffusion tensor imaging, susceptibility-weighted imaging, perfusion-weighted imaging, chemical shift imaging, and intra-voxel incoherent motion, and their variations. For example, the MRI system 10 acquires radiological images 310, 320 in FIGS. 3A and 3B.

In step 820, the MRI system 10 conducts image preprocessing to remove the regions of non-interests in radiological images.

Figure 10:
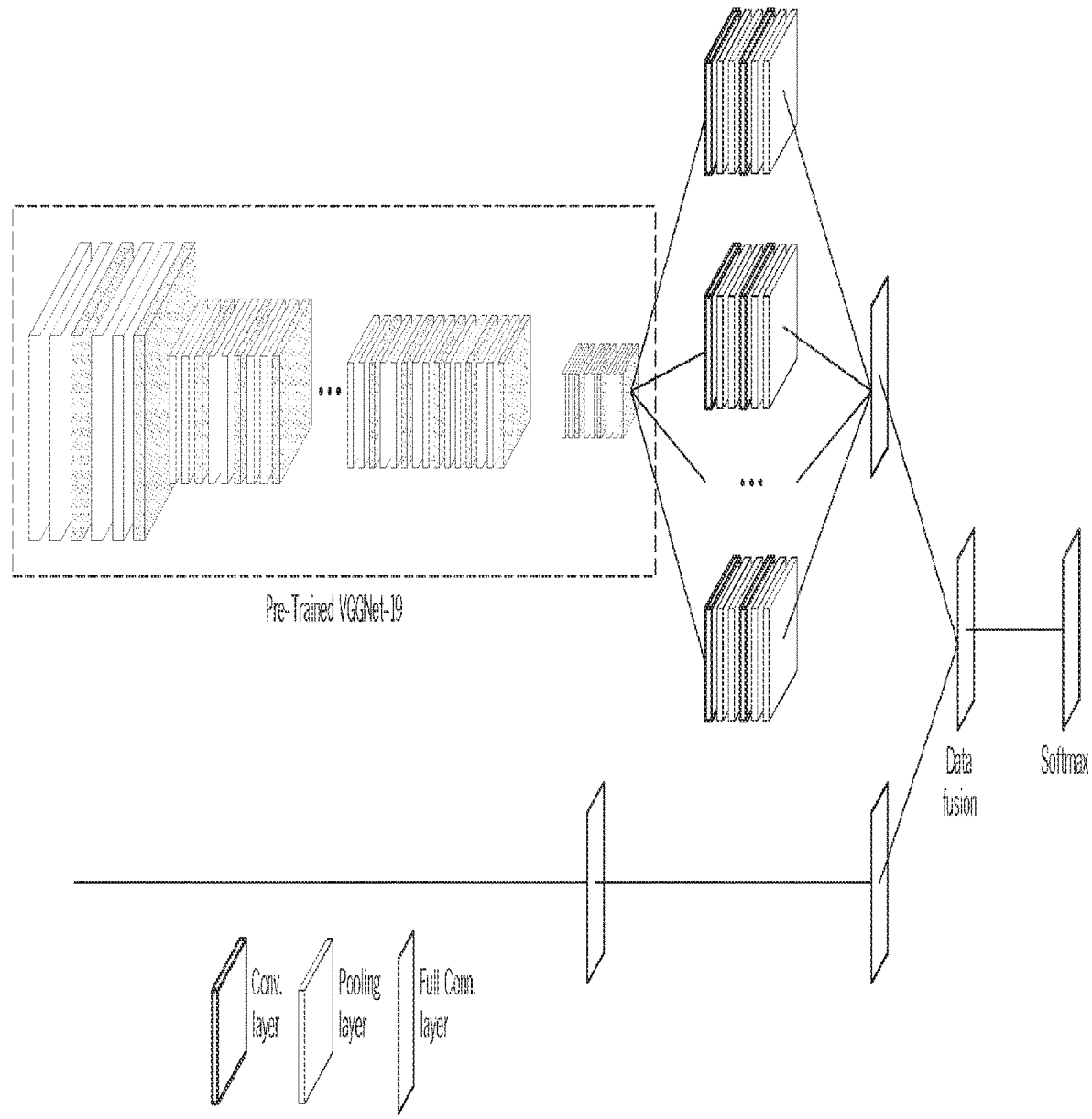
FIG. 10 depicts an exemplary deep learning model.

In step 830, the MRI system 10 trains a deep learning model using a labeled data set (molecular or genetic subtypes, normal tissue cells, inflammatory cells) from histopathological exams and the preprocessed radiological images. FIG. 10 depicts an exemplary deep learning model.

In embodiments, a deep transfer learning model may be utilized to accurately predict clinical outcome in patients with ICH (e.g., at 3 months) using the integration of clinical and FLAIR imaging data. The deep learning model may include two separate input channels, one for imaging and the other for clinical data. To extract high-level discriminative imaging features in imaging channel, a module with 24 layers may be designed by reusing the weights of a pre-trained VGG-19 model (1st to 21st layers), and then the weights of two additional convolutional layers with [64, 128] neurons and 3×3 filters and one fully-connected layer with 64 neurons is trained. For each patient, the model analyzed n=8 slices containing the entire hemorrhagic lesion. For the clinical channel, one fully-connected layers with 64 neurons was applied to learn the discriminative features from the clinical data. Finally, a fully connected fusion layer with 64 neurons was applied to integrate the extracted discriminative information from both imaging and clinical data. A two-way softmax classifier was then utilized to identify the patients likely to have unfavorable outcomes. Rotation and shift-based data augmentation strategy was implemented to increase the training samples by 10 times (but not testing samples). As a result, the present model may correctly identify patients likely to have unfavorable outcomes with an AUC of 0.87 (95% confidence interval: 0.86, 0.89).

In step 840, the MRI system 10 classifies molecular or genetic subtypes of tumor in the radiological images using a classifier of the deep learning model and identifying intra-site tumor heterogeneity based on the classified cells. In some embodiments, the classifier is an unsupervised clustering algorithm/model, which can identify multiple cell types with or without genetic heterogeneity in high dimensional image feature space. In some embodiments, the classifier is a supervised classification algorithm/model, which is trained on a set of image features derived from acquired high resolution images of preselected patient populations or simulated images with the specific molecular or genetic subtypes. The trained model is fine-tuned and validated on a separate independent set of images. Finally, another independent set of images is used to test the model and report final statistical results. It is noted that each of the three sets of images should be independent, without overlap.

Figure 9A:
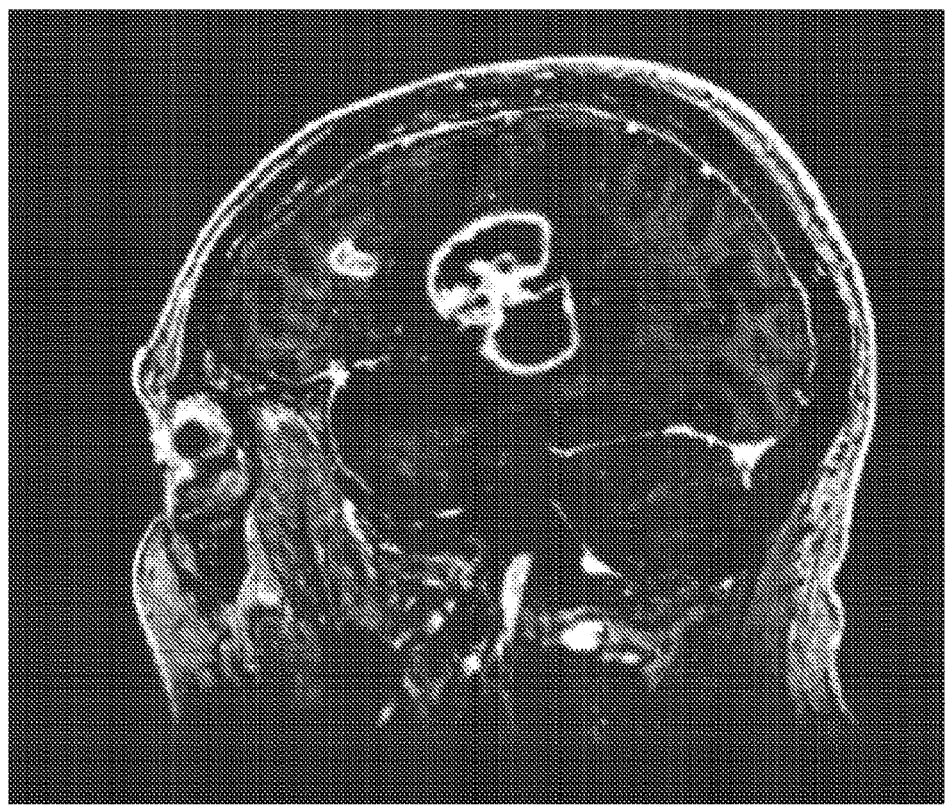
FIG. 9A depicts an example of an input for a deep learning model.
Figure 9B:
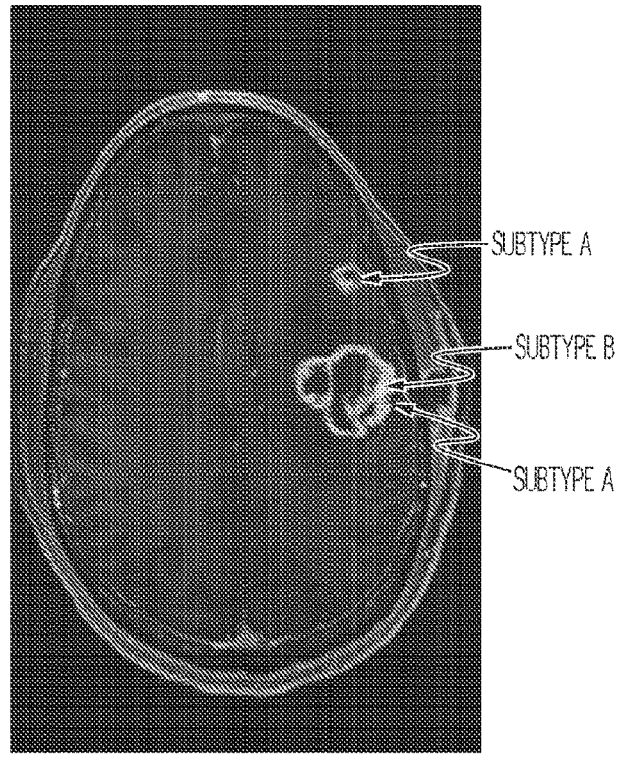
FIG. 9B depicts an example of an output image for the deep learning model.

FIG. 9A depicts an example of an input for a deep learning model. More specifically, it is a post-contrast T1-weighted imaging of a patient with Glioblastoma Multiforme. FIG. 9B depicts an example of an output image for the deep learning model. More specifically, the output image includes two tumor sites. Each tumor site includes the own intra-site tumor heterogeneity. The different colors represent different molecular or genetic subtypes, such as IDH-wild or IDH-mutant. For example, tumor cells having molecular or genetic subtypes of genetic type A are illustrated in blue, and tumor cells having molecular or genetic subtypes of genetic type B are illustrated in yellow.

To date, most research applications of AI in brain tumors have focused on addressing challenges in distinguishing between histopathologic and molecular subtypes of brain tumors. Machine learning algorithms are trained using the MRI images of preselected patient populations with the specific tumor subtypes. Contacting the quantitative image biomarkers derived from the acquired images with the specific genetic or molecular profiles.

The present method holds a great promising in diagnosis, treatment assessment, the development of anti-cancer therapy, and outcome prediction of brain tumor.

First, the identification of genetic or molecular profiles is a fundament input for precision medicine of a tumor. It is well known that precision medicine may greatly improve outcome of cancer patients. However, there is a significant amount of intra-tumor heterogeneity in terms of gene expression, genotype, and molecule phenotype. The identification of intra-site tumor heterogeneity may provide key information for target therapies. In present clinical practices, a single tumor site is assumed to be homogeneous though a lot of histopathological exams demonstrate the existence of intra-site tumor heterogeneity. The use of the identifying intra-site tumor heterogeneity of driver mutations may be critical for selecting optimal targeted therapy. In some embodiments, the measurement of intra-site tumor heterogeneity is employed to select optimal targeted therapy.

Second, monitoring the intra-site tumor heterogeneity during treatment and follow-up may assess the treatment response timely, non-invasively and accurately. The intra-tumor heterogeneity is sensitive to anti-cancer therapy, and may be linked to clinical outcomes. For example, an increase in intra-tumor heterogeneity may be linked to cancer progression. The intra-site tumor heterogeneity may characterize the response of different genetic or molecular profiles on a given therapy. This may be used to study the effect of a novel therapy on the different genetic or molecular profiles, and then identify the novel therapy as a precision medicine of patients with a specific genetic and molecular profile. In some embodiments, the identification of intra-site tumor heterogeneity over time may be implemented to evaluate and develop the targeted therapy.

Third, the intra-site tumor heterogeneity may be used to study treatment resistance mechanism locally because there is extensive heterogeneity of a tumor site. The identification of intra-site tumor heterogeneity over time may monitor the genetic evolution of tumor or tumor recurrence, uncovering the treatment resistance mechanism.

Finally, various cancer treatments may result in increased heterogeneity within the tumor, leading to the evolution of multiple resistance mechanisms. Real time monitoring the intra-site tumor heterogeneity holds a potential to timely adjust treatment strategies for the reduction of the heterogeneity, leading to improvement of long-term therapeutic responses.

In summary, the present disclosure provides a rapid, non-invasive, repeatable, and effective method to identify the intra-site tumor heterogeneity without causing unwanted changes to the cellular genetic profile. The present method holds a great promising in diagnosis, treatment assessment, the development of anti-cancer therapy, and outcome prediction of brain tumor.

In some embodiments, the present method may identify the intra-site tumor heterogeneity of various brain metastases, including prostate cancer, malignant pleural mesothelioma, non-small cell lung cancer, gastrointestinal stromal tumor, soft tissue sarcoma, neuroendocrine tumors, disseminated pediatric malignant, and primary brain tumors.

In some embodiments, the present method can identify the intra-site tumor heterogeneity of primary brain tumors, including gliomas, meningioma, pituitary adenomas, etc.

In some embodiments, the present methods described herein may include the quantification of a particular genetic or molecular types within a tumor site. In these embodiments, the methods include differentiating the presence of one or more cancer cells in the region of interests, where the differentiation is made based on the radiomic feature derived from the obtained image data.

In some embodiments, it should be understood that this disclosure should include all MRI image modalities, such as T1-weighted imaging, T2-weighted imaging, diffusion, diffusion tensor imaging, susceptibility-weighted imaging, perfusion-weighted imaging, chemical shift imaging, intravoxel incoherent motion, but not limit to, and their combinations with and/or without the administration of contrast agent. As a result, this disclosure provides non-invasive, safer, faster, accurate, earlier, more effective method and system for identifying the intra-tumor heterogeneity in all research, drug development and clinical practices.

Optionally, image modalities include 2 dimensional or 3 dimensional imaging acquisition in space.

Optionally, the region of interest may include at least one of a lesion, a landmark, a texture, or a feature of interest.

The invention claimed is:

1. A method for measuring intra-site heterogeneity in a tumor using magnetic resonance imaging (MRI), the method comprising:
   acquiring one or more magnetic resonance (MR) images of a region of interest including the tumor using at least one MRI modality;
   segmenting one or more tumor sites in the MR images;
   dividing each of the one or more tumor sites into a plurality of sub-regions;
   deriving image biomarkers from each voxel or pixel in each of the plurality of sub-regions;
   classifying each voxel or pixel in each of the plurality of sub-regions into one of genotypes or molecular subtypes based on the derived image biomarkers and a classifier model including associations between image biomarkers and genotypes or molecule subtypes;
   creating a distribution of genotypes or molecular subtypes in the each of the plurality of sub-regions based on classifications of voxels or pixels in each of the plurality of sub-regions;
   generating spatial information of genotypes or molecular subtypes in the tumor sites based on the distribution of the genotypes or molecular subtypes in the plurality of sub-regions; and
   measuring intra-site heterogeneity in the tumor sites based on the spatial information.

2. The method of claim 1, wherein the tumor is primary brain tumors or brain metastases.

3. The method of claim 1, wherein the intra-tumor heterogeneity in the tumor sites comprises different genetic or molecular characterizations within the tumor sites, including one or more of molecules, gene expressions, or mutations.

4. The method of claim 1, wherein the MR image is acquired by magnetic resonance imaging sequences with or without administration of a contrast agent.

5. The method of claim 4, wherein magnetic resonance imaging sequences include one of T1-weighted imaging, T2-weighted imaging, diffusion-weighted imaging, functional MR imaging, diffusion tensor imaging, susceptibility-weighted imaging, perfusion-weighted imaging, chemical shift imaging, and intra-voxel incoherent motion, and their variations.

6. The method of claim 1, wherein a spatial resolution of the one or more MR image is less than 2.0 milliliter.

7. The method of claim 1, wherein a spatial resolution of the one or more MR images is less than 1.0 milliliter.

8. The method of claim 1, wherein a spatial resolution of the one or more MR images is less than 0.2 milliliter.

9. The method of claim 1, wherein the sub-region of the tumor site includes at least 100 pixels or voxels.

10. The method of claim 1, wherein the sub-region of the tumor site includes at least 20 pixels or voxels.

11. The method of claim 1, wherein the sub-region of the tumor site includes at least 8 pixels or voxels.

12. The method of claim 1, wherein the image biomarkers include tissue properties or image features derived from the acquired MR image;
   wherein the tissue properties include at least one of T1, T2, proton density, perfusion, cerebral blood volume, oxygen concentration, permeability, iron concentration, and diffusion coefficient; and
   wherein the image features include at least one of size and shape based-features, descriptors of the image intensity histogram, descriptors of the relationships between image voxels including a gray-level co-occurrence matrix (GLCM), run length matrix (RLM), size zone matrix (SZM), and neighborhood gray tone difference matrix (NGTDM) derived textures, textures extracted from filtered images, and fractal features.

13. The method of claim 1, wherein a biophysical model is used to associate each of the image biomarkers with a specific genotype or molecule subtype.

14. The method of claim 1, wherein the classifier model comprises either a supervised model or an unsupervised model;
   wherein the supervised model further comprises support vector machines, linear regression, logistic regression, naive Bayes, linear discriminant analysis, decision trees, k-nearest neighbor algorithm, similarity learning and their variations; and
   wherein the unsupervised model further comprises Clustering analysis, sample specificity learning, self-supervised learning, and Generative models.

15. The method of claim 1, wherein the classifier model comprises one or more of machine learning models, including support voting machine (SVM), a naive Bayes classifier, a decision tree, a boosted tree, a random forest classifier, a fuzzy logic classifier, a neural network, a nearest neighbor classifier, deep learning, and a nonlinear classifier.

16. The method of claim 1, wherein the classifier model is trained by image biomarkers derived from a plurality of training images and ground truth of cancer patients with specific genetic or molecular data; and
   wherein each of the plurality of training images corresponds to one or more patients with the tumor.

17. The method of claim 1, further comprising: determining the genotype of each voxel or pixel in each of the plurality of sub-regions with an area under the curve (AUC) of greater than 0.95.

18. The method of claim 1, further comprising: determining the genotype of each voxel or pixel in each of the plurality of sub-regions with an area under the curve (AUC) of greater than 0.8.

19. The method of claim 1, wherein classifying each voxel or pixel in each of the plurality of sub-regions into one of genotypes or molecular subtypes is determined based on a probability of the voxel or pixel being classified into one of genotypes or molecular subtypes.

20. A system for measuring intra-site heterogeneity in a tumor using magnetic resonance imaging (MRI), the system comprising:
   a receiver configured to acquire one or more magnetic resonance (MR) images of a region of interest including the tumor using at least one MRI modality; and
   a processor configured to:
      segment one or more tumor sites in the MR images;
      divide each of the one or more tumor sites into a plurality of sub-regions;
      derive image biomarkers from each voxel or pixel in each of the plurality of sub-regions;
      classify each voxel or pixel in each of the plurality of sub-regions into one of genotypes or molecular subtypes based on the derived image biomarkers and a classifier model including associations between image biomarkers and genotypes or molecule subtypes;
      create a distribution of genotypes or molecular subtypes in the each of the plurality of sub-regions based on classifications of voxels or pixels in each of the plurality of sub-regions;

generate spatial information of genotypes or molecular subtypes in the tumor sites based on the distribution of the genotypes or molecular subtypes in the plurality of sub-regions; and measure intra-site heterogeneity in the tumor sites based on the spatial information.

\* \* \* \* \*